(12) United States Patent
McGusty et al.

(10) Patent No.: US 8,626,262 B2
(45) Date of Patent: Jan. 7, 2014

(54) PHYSIOLOGICAL DATA COLLECTION SYSTEM

(75) Inventors: Edwin A. McGusty, Land O'Lakes, FL (US); John W. Parker, III, Clearwater, FL (US); Michael J. Vosch, Titusville, FL (US)

(73) Assignee: Halthion Medical Technologies, Inc., Tampa, FL (US)

( * ) Notice: Subject to any disclaimer, the term of this patent is extended or adjusted under 35 U.S.C. 154(b) by 232 days.

(21) Appl. No.: 13/153,825

(22) Filed: Jun. 6, 2011

(65) Prior Publication Data

US 2011/0237924 A1    Sep. 29, 2011

Related U.S. Application Data

(63) Continuation-in-part of application No. 10/476,437, filed on Oct. 30, 2003, now Pat. No. 7,970,450.

(51) Int. Cl.
*A61B 5/0402* (2006.01)
*A61B 5/0408* (2006.01)

(52) U.S. Cl.
USPC ............ 600/391; 600/392; 600/393; 600/509

(58) Field of Classification Search
USPC ......................................... 600/391–393, 509
See application file for complete search history.

(56) References Cited

U.S. PATENT DOCUMENTS

| | | | |
|---|---|---|---|
| 3,888,240 A * | 6/1975 | Reinhold et al. | 600/390 |
| 4,331,153 A | 5/1982 | Healy | |
| 4,353,372 A * | 10/1982 | Ayer | 600/393 |
| 4,850,370 A | 7/1989 | Dower | |
| 5,042,481 A * | 8/1991 | Suzuki et al. | 600/393 |
| 5,184,620 A | 2/1993 | Cudahy et al. | |
| 5,626,135 A | 5/1997 | Sanfilippo | |
| 5,730,143 A | 3/1998 | Schwarzberg | |
| 5,788,633 A | 8/1998 | Mahoney | |
| 5,938,597 A | 8/1999 | Stratbucker | |
| 5,995,861 A | 11/1999 | Price | |
| 6,117,077 A | 9/2000 | Del Mar et al. | |
| 6,289,238 B1 | 9/2001 | Besson et al. | |
| 6,385,473 B1 * | 5/2002 | Haines et al. | 600/393 |
| 6,400,975 B1 | 6/2002 | McFee | |
| 6,415,169 B1 | 7/2002 | Kornrumpf et al. | |
| 6,416,471 B1 | 7/2002 | Kumar et al. | |
| 6,450,953 B1 * | 9/2002 | Place et al. | 600/300 |
| 6,453,186 B1 * | 9/2002 | Lovejoy et al. | 600/386 |
| 6,494,829 B1 * | 12/2002 | New et al. | 600/300 |
| 6,847,836 B1 * | 1/2005 | Sujdak | 600/382 |
| 6,856,832 B1 * | 2/2005 | Matsumura et al. | 600/523 |
| 7,266,405 B1 | 9/2007 | Alroy et al. | |
| 7,286,865 B2 | 10/2007 | Nazeri | |
| 7,444,177 B2 * | 10/2008 | Nazeri | 600/382 |
| 7,542,878 B2 | 6/2009 | Nanikashvili | |
| 8,019,402 B1 * | 9/2011 | Kryzpow et al. | 600/386 |
| 2006/0030782 A1 * | 2/2006 | Shennib | 600/509 |
| 2006/0155183 A1 | 7/2006 | Kroecker et al. | |
| 2008/0154110 A1 * | 6/2008 | Burnes et al. | 600/382 |
| 2011/0021937 A1 | 1/2011 | Hugh et al. | |

* cited by examiner

*Primary Examiner* — Lee S Cohen
(74) *Attorney, Agent, or Firm* — Lonnie Drayer

(57) ABSTRACT

A physiological data collection system facilitates acquiring, recording, transferring and analyzing physiological signals generated from the skin of a human subject that may be used in generating an electrocardiogram for a patient in a continuous manner over an extended period of time of twenty four to forty eight hours. The physiological data collection system is an assembly of a disposable physiological sensor device and a reusable data collection module. Collected physiological data may be transmitted for analysis via either a cable or a wireless communication system.

19 Claims, 14 Drawing Sheets

PHYSIOLOGICAL DATA COLLECTION SYSTEM

CROSS REFERENCE TO RELATED APPLICATION

This application is a continuation -in-part of application Ser. No. 10/476,437, filed Oct. 30, 2003, now U.S. Pat. No. 7,970,450.

FIELD OF THE INVENTION

The present invention relates to a device that is a system for collecting physiological data from a human subject in a continuous manner over an extended period of time of twenty four to forty eight hours. The physiological data collected by the system may be used in generating an electrocardiogram for the human subject.

BACKGROUND OF THE INVENTION

The ability to obtain electrical activity of the human heart from the surface of the skin that was effectuated by Augustus De'sire Waller in 1887 required the subject's limbs to be submersed in saline. In 1912 Willem Einthoven defined lead positions I, II and III which became known as Einthoven's Triangle. The use of physiological sensors or chest leads for the purpose of collecting electrical data generated by a person's heart in a clinical environment dates back to Charles Wolferth and Francis Wood in 1932. This led to the Wilson Central Terminal, an "indifferent electrode (neutral or grounding electrode)" by Frank Wilson in 1934, and standardized positions and wiring of the chest leads V1-V6 in 1938 that were adopted by the American Heart Association. In 1942 Emanuel Goldberger added limb leads aVR, aVL and aVF, which when combined with leads I-III and V1-V6, create the twelve lead electrocardiograms in use today. Robert Zalenski defined what is now known as leads V4R, V8 and V9 in 1993 creating the 15 lead ECG.

In 1949 physicist Norman Holter invented in the first telemetric cardiac monitoring device or ambulatory electrocardiography device known as the "Holter Monitor". The original "Holter Monitor" weighed seventy-five pounds. After significant size and weight reductions, it began usage in mainstream clinical environments in the 1960's. The typical "Holter Monitor" in use today weighs less than six ounces and is the most prevalent device used for the diagnosis and monitoring of cardiovascular conditions.

The object of a Holter test is to record the electrical activity of a person's heart for a continuous period of time which ranges between twenty-four and forty-eight hours. It is further the goal to have the test completed while the person conducts his normal daily activities while wearing the testing device. Unfortunately, typical devices in use today are not easily concealed and require placement and hook up onto the person by a skilled technician. They are uncomfortable and restrictive in one's ability to carry out day to day tasks and for sleeping while the test is carried out. As such, it is well known to those in the medical community that patient compliance is minimal at best and a large percentage of patients will call out sick from work or restrict their activities during the testing period. This leads to data being collected in a hybrid situation since it is a variance of the desired daily activity. While the present invention is not specific or limited only to use during ambulatory electrocardiographic testing or Holter Monitoring, a primary use of the present invention is for such monitoring.

The field of electrocardiogram (ECG) testing is comprised of devices that use anywhere from a single channel of data consisting of the placement of two electrodes on a patient's body to a plurality of electrodes that may number as many as eighteen individual electrodes to produce a sixteen lead ECG and any variation in between. Additionally, there exists within the industry numerous algorithms or methods used to obtain ECG's of different lead counts using fewer actual leads attached to the patient. Examples of such algorithms or methods include MEANS and EASI which allow the production of a twelve lead ECG from only three channels of collected data. The EASI method developed by Gordon E. Dower (disclosed in U.S. Pat. No. 4,850,370) derives a twelve lead ECG from the placement of electrodes using lead positions E, A, S and I in addition to a common ground as derived by Ernest Frank Ph.D. in 1956.

Further attention is directed to the state of the current healthcare system in place in the U.S.A. today. The Centers for Disease Control and Prevention (CDC) estimates that the total cost of Healthcare in 2010 surpassed two and a half trillion dollars and that the portion of that sum relating to the diagnosis, treatment and monitoring of cardiovascular related illnesses and diseases exceeds five hundred billion dollars. A significant focus is being placed on the need to establish earlier detection methods while at the same time reducing the costs associated with diagnosis, treatment and monitoring of cardiovascular related illnesses and diseases. One method of accomplishing these goals is to place more devices in the market that do not rely on costly manufacturing methods or need highly trained and costly medical professionals for the use of the devices. The invention described herein accomplishes both of these goals while providing many other benefits to devices currently used in the market place.

DISCUSSION OF THE PRIOR ART

There are two aspects to the process of obtaining biological data, such as an electrocardiogram (ECG), from patients for use in assessing a patient's health—first the gathering of the data and second the transmittal of the data to a person or machine for analysis.

Ambulatory monitors collect data from a patient via a single patch or multiple patches containing sensors or electrodes that collect the electrical and other biological data from the patient. In single sensor electrode patches, a patient will have anywhere from two to as many as sixteen of the single sensor electrode patches on his person during the testing period. An example of such an electrode is disclosed in Healy, U.S. Pat. No. 4,331,153, or Sanfilippo, U.S. Pat. No. 5,626, 135. Both Healy and Sanfilippo are snap electrodes while Sanfilippo also has the ability to be used as a tab electrode or in a combination of both snap and tab electrodes simultaneously. Both snap and tab electrodes are well known to those skilled in the art. These electrodes are prone to artifacts (spurious signals) due to movement between an electrode contactor or fastener and a lead wire or cable extending from the electrode. They are also highly prone to detachment of the electrode from the lead wire or connecting cable during the testing period from tension placed on the lead wire or connecting cable attached to the electrode. Additionally repeated use of the lead wires leads to non secure connections to the electrodes which can result in incomplete or inaccurate data collection. Each of these known issues with these devices can violate the integrity of the test being performed and potentially forces the patient to begin testing again from the start.

Sensor arrays or patches containing a plurality of sensors are also well known to those skilled in the art. Examples of such devices are disclosed in Cudahy et al., U.S. Pat. No. 5,184,620, Stratbucker, U.S. Pat. No. 5,938,597 and Sujdak, U.S. Pat. No. 6,847,836. These patches vary in size depending upon the number of functions or tasks they attempt to perform and can be rather bulky in size and reduce or impede the mobility of a patient during the testing period. In Cudahy et al, U.S. Pat. No. 5,184,620, the device has an electrode assembly that includes a pad containing six groups of electrodes arranged in rows of two electrodes each. The electrodes are labeled from left to right and from top to bottom in each row as LA, V1, GRND, V2, S1, V3, V4, LL, S2, V5, RA and V6. Electrode LA is in close proximity to the left arm, while electrode RA is positioned such as it is close in proximity to the right arm. Stratbucker, U.S. Pat. No. 5,938,597, teaches a bioelectric interface comprised of a plurality of electrodes that are fixed to a support sheet in a desired spatially separated pattern such that in use the electrodes are essentially fixed in location with respect to one another. The Stratbucker device contains eighteen electrodes that are in contact with a subject's skin, one each of LA, RA, LL, V1, V2 and V3; three each V4, V5, V6 and RL. In each of the cited devices, the placement of the patch covers the majority of the test subject's chest area. Sujdak, U.S. Pat. No. 6,847,836, teaches a patch containing ten electrodes that are divided into two groups, each connected to a separate wiring harness. A first section contains electrodes providing data from V1, V2, V3, V4, V5 and V6 connected to a first wiring harness. A second section contains electrodes providing data from RA, LA, RL and LL connected to a second wiring harness. The wiring harnesses would then be connected via direct cabled coupling to the ECG machine. Sudjak further teaches that the two sections are able to be used in conjunction with each other to provide data for a conventional twelve lead ECG or separate from each other independently. Sudjak further teaches that to be effective for use, the device would have to be produced in five separate sizes to accommodate the varying sizes of persons it is intended for use with.

Prior art devices such as those taught by Cudahy and Stratbucker are more suited for use by a male test subject than by a female test subject. In female test subjects proper electrode placement is further complicated by the breasts. Because breast sizes vary greatly amongst females this issue is further exacerbated. While neither Cudahy nor Stratbucker address this known issue, Nazeri, U.S. Pat. No. 7,286,865, references "consideration for gender" and only teaches "pads for males are likely to be larger than those for females." Alroy et al, U.S. Pat. No. 7,266,405, teaches "Furthermore, owing to anatomical differences between men and women, different electrode assemblies are preferably supplied to men and women". Alroy et al fails to teach any specifics as to what different forms devices for male and female test subjects should take.

The prior art also teaches patches or overlays containing a plurality of sensors where the sensors are not permanently fixed in position and are therefore adjustable to the point of attachment to the patient's skin to some varying degrees. Examples of such are found in Mahoney, U.S. Pat. No. 5,788,633, Price, U.S. Pat. No. 5,995,861, and Kornrumpf et al, U.S. Pat. No. 6,415,169. Each of these publications teaches the recording of data from lead positions V1, V2, V3, V4, V5 and V6. Mahoney and Price require the use of standard single electrode patches in conjunction with their use, with Mahoney requiring four and Price requiring six electrodes. Mahoney teaches that ECG data collected via the electrodes from the test subject is channeled from lead traces contained within the device to a single connector on the harness which replaces individual lead wires used in conventional ECG tests. Price is an overlay to aid in the correct positioning of electrodes on the patient for ECG test purposes and normal lead wires are still used. Price teaches a reusable patient specific platform in which the included electrodes slide along a web of trace leads and are locked into place when a correct position is determined. Each are highly subject to artifacts as previously disclosed herein. Kornrumpf et al teaches the addition of leads RA, LA, RL and LL which are adjustable in their respective placements.

Both single and multiple sensor patches in the prior art are simply methods for collecting physiological data from the patient that must then be transferred to some other device for storage and or processing. This transfer is either completed thru a direct coupling of the sensors via wires or via a wireless method to a remote data storage or collection device.

Prior art sensor arrays or patches whose data transmission is conducted via direct coupling are disclosed in McFee, U.S. Pat. No. 6,400,975, and Suzuki et al, U.S. Pat. No. 5,042,481. FIG. 3 of McFee discloses a coupling device that requires individual connection of the twelve lead wires to a monitoring device. In the case of individual lead wire connections there is a significant likelihood of the lead connections being placed in the wrong locations which provides inaccurate test data. A coupler 15 is specified in FIGS. 4 and 6 of Suziki et al, but the structure of the coupler 15 is not disclosed. In both of these devices the coupling wires are known to be uncomfortable, difficult to keep untangled and prone to detachment.

Prior art sensor arrays or patches that transmit data wirelessly require additional electronic components that are either externally connected such as disclosed by Haines, et al, U.S. Pat. No. 6,385,473, or are contained within the patch as disclosed by Besson et al, U.S. Pat. No. 6,289,238. In Haines the physiological sensor device or array includes an array of sensors (Device 10) which generate data about the physiological condition of a subject. This data is transmitted to a portable transfer unit (12) which while not disclosed is attached to Device 10 and is also attached to the body of a test subject occupying additional surface area on the test subject. In Besson et al circuitry is embedded into the patch. In a single use disposable situation cost for production and usage of the device is significantly higher than that of devices such as Haines. Besson et al shows in FIG. 3 a multitude of individual patches placed on a single test subject for the collection of physiological data.

In the case of neonatal patients or infants, the overwhelming majority of current methods and means of obtaining electrocardiographic (ECG) data from such patients relies upon devices that are intended for use on adult patients. While infant specific devices are rare, one such device is disclosed in Lovejoy et al, U.S. Pat. No. 6,453,186. The Lovejoy et al device teaches a patch with a plurality of electrodes that is directly coupled to an ECG machine and is not suitable for use in an ambulatory environment.

All of the prior art electrode patches that have been discussed herein require additional time to prep for use and would be difficult to use by a person unskilled or untrained in the medical field for which use of the prior art electrode patches is intended.

As pointed out at the beginning of this section the second aspect to the process of obtaining physiological data from patients for use in assessing a patient's health involves the transmittal of the data collected to a person or machine for analysis of the data. There are three classes of devices for providing this function. The first and most prevalent class of devices in the market is standard "Holter Monitors" that are discussed above. These devices are worn for a continuous period of time by the patient, typically 24 to 48 hours in length, and after the testing period has been completed, the device is returned to the ordering physicians office where the recorded data is retrieved, processed, analyzed and a report is generated.

The second category of ambulatory ECG devices include a base station module which wirelessly receives the collected data from the module worn by the patient and then telephonically transmits the data to the ordering physician's office or a data center for processing and analysis. Like standard "Holter Monitors" described above, the use of individual electrodes, connecting lead wires and recording modules worn on the waist or belt are also required.

The third category of ambulatory ECG devices has the ability to wirelessly transmit the collected data to a remote data center for processing, analysis and reporting. These devices either use the standard electrodes and lead wires as previously disclosed, or sensor arrays or patches that contain a plurality of electrodes for obtaining the physiological data from the patient. While these devices allow for greater mobility of the patient than the previous discussed device, they still have a data collection module that is physically connected to the electrodes or patch in addition to a device that contains cell phone technology that receives data from the collection module and then wirelessly transmits said data to the remote data center. An example of one such device can be found in Hugh et al., US 2011/0021937 A1. In addition to the known problems as previously disclosed herein, this category of devices requires that the patient remain in close proximity to the remote transmitting device typically within thirty feet. A well known issue to those within the medical community with regard to the use of these devices is that the patient unintentionally leaves the active monitoring zone which interrupts data collection and forces the test to be restarted, wasting valuable time and delaying results.

In U.S. Pat. No. 7,542,878 B2 Nanikashvili discloses a system that utilizes electrodes or sensor devices that are placed on a patient's chest to collect physiological data from the patient. This data is then transferred by either a direct coupling or wireless means to a cell phone or personal data assistant (PDA) where the collected data is then processed by a program on the phone or PDA and subsequently transmitted to a remote medical center. Like so many other devices in the current marketplace, Nanikashvili relies on the use of a cell phone or PDA to store, process and transmit the data to the remote medical center. The present invention eliminates in its entirety the cell phone or PDA and places the processor, nonvolatile memory and the wireless capabilities such as cellular (CDMA, GSM HSPA +, or LTE), ANT+, Bluetooth, WiFi or WiMax.directly into the data collection module. While the Nanikashvili device runs health monitoring software to process the physiological data, the present invention amplifies and converts the analog data to a digital format and then stores it in an unaltered form for transmission to the remote monitoring and analysis facility for processing, analysis and interpretation.

Schwarzberg teaches in U.S. Pat. No. 5,730,143 the merging or combining of the typical ambulatory recorder or Holter Monitor and the typical event monitor into a single device. Like the Nanikashvili device, there is present within the device a program or coding that monitors and analyzes the collected physiological data for the occurrence of what Nanikashvili defines as a "clinically significant cardiac event", which then requires the device to be brought to a remote station for evaluation, or the patient must transmit by "telephonic communication" the collected data for evaluation. In either method the patient is required to intervene to facilitate the transfer of data for evaluation. The present invention does not analyze, monitor or screen the physiological data being collected for the occurrence of any clinically significant cardiac events. The present invention does not require any interaction from the patient for transmission of the physiological data for analysis, review and interpretation, in that it is done automatically using the included wireless transmitter contained within the device.

Del Mar, et al. in U.S. Pat. No. 6,117,077 discloses a device designed as a self contained ambulatory physiological recorder. In a preferred embodiment it has three electrodes with one being designated as a ground. The Del Mar, et al. device has several significant drawbacks or limitations as compared to the present invention. One drawback is the limiting factor of having only three electrodes. While the ability to add additional electrodes is possible, it requires the connection of a pigtail to the main body of the device that contains the additional lead cables. The use of the device on both male and female patients is only accomplished through the use of two separate and distinct embodiments. Del Mar, et al. teach "a perspective view of a second embodiment of the invention uniquely designed to adapt to a female torso . . . " is shown in their FIG. 5. This defeats the cost and inventory reduction goals of the Del Mar, et al. device in that multiple devices for both male and female patients must be maintained. Additionally, the event button is located below the surface of the device and according to the illustrations no identification of its existence is present to alert the patient to its appropriate use.

A significant concern the healthcare Industry in the United States of America faces today is rising costs and reduced reimbursement rates. Currently available devices fall within two distinct categories. In the first category the entire device is single use and is disposed of in its entirety after the testing period is complete. Examples of these devices can be found in Kroecker et al., US 2006/0155183 A1, and Besson et al., U.S. Pat. No. 6,289,238 B1. The disadvantages associated with Kroecker and Besson are that cost of use for each individual test to be completed is elevated in that the electronics required to collect and transmit the physiological data from the patient are incurred each time a test is run. In the second category are devices where the electronics for collection are reusable and attach to the single use sensor array or patches. Examples of such a device can be found in Kumar et al., U.S. Pat. No. 6,416,471 B1. The Kumar et al. device utilizes a patch or sensor array that resides across the majority of the patient's chest and then must be coupled to an electronics module that is also attached to the patient's chest taking up additional surface area. This device still requires the use a receiving module that is kept on or near the patient's body. One major downside to this type of product is that the amount of surface area and equipment required to be placed on the patient's chest is significantly greater than that of a device according to the invention disclosed herein. Additionally, the Kumar et al. device would be very cumbersome for use by a female patient given the placement challenges posed by the breasts.

SUMMARY OF THE INVENTION

The physiological data collection system of the present invention relates to a system and method of acquiring, recording, transferring and analyzing physiological signals generated from the skin of a human subject such that would be used in generating an electrocardiogram (ECG/EKG) for the patient in a continuous manner over an extended period of time of twenty four to forty eight hours. An electrocardiogram (ECG/EKG) produced using the physiological data collection system of the present invention is an industry accepted and recognized multi-lead ECG that is accurate, cost effective, consistent and easily attachable by a person who is unskilled or untrained in the medical field.

The physiological data collection system of the present invention collects data from a patient through the combined use of a disposable single use physiological sensor device or patch containing a plurality of electrodes, along with a reusable, rechargeable data collection module that is directly coupled to the disposable physiological sensor device or patch that is capable of acquiring, recording, storing and in the preferred embodiment, transmitting by a wireless means, the data necessary to a remote data monitoring center for analysis and review.

The physiological data collection system and method of the present invention has two distinct and separate components. The first component is a disposable physiological sensor device or patch, an example of which is disclosed herein. The second component is a rechargeable and reusable data collection module, an example of which is disclosed herein, that is directly coupled and attached to an outer surface of the physiological sensor device or patch. When properly coupled together and appropriately attached to a patient's skin in the correct location the two components working together create and comprise the physiological data collection system and method of the present invention.

It is an advantage of the physiological data collection system of the present invention that it may be used in both an ambulatory and "in office/in hospital" environments.

It is another advantage of the physiological data collection system of the present invention that the patient or another person who is not highly skilled or highly trained by the medical community can attach the system to the skin of the patient.

It is another advantage of the physiological data collection system of the present invention that it ensures the proper and consistent placement of the system on a patient for accurate and consistent data collection and this may be repeated if necessary.

It is a further advantage of the physiological data collection system of the present invention to reduce the total cost associated with the production of a multi-lead physiological data collection system ECG from manufacture thru placement on the patient.

It is still another advantage of the physiological data collection system of the present invention that data retrieval or collection of the physiological data contained within the data control module may be effected by either direct coupling to a personal computer or a by wireless transmission to a remote monitoring and analysis center.

It is still another advantage of the physiological data collection system of the present invention that it may be worn and used by a patient while conducting his or her normal daily routine without delay or interference from the invention.

It is still another advantage of the physiological data collection system of the present invention that it is not gender specific and the same system may be worn by either a man or a woman with no discernable difference in the physiological data being collected from the patient.

It is still another advantage of the physiological data collection system of the present invention the data collection module is provided with an "event button" that may be pushed by a patient who experiences symptoms of a cardiac event thereby prompting the data control module to preserve physiological data relating to the event. If the module has wireless capabilities, the collected and recorded physiological data pertaining to the event may be immediately transmitted by wireless means to the remote monitoring and analysis center for immediate review and interpretation.

It is still another advantage of the physiological data collection system of the present invention that in when the system is provided with an alternative embodiment of the data control module the system can a person can interact with the data collection module to configure certain properties and or configurations of the testing procedure or procedures being conducted during the testing period.

It is still another advantage of the physiological data collection system of the present invention that because it is a self contained apparatus the reliability, accuracy and integrity of the collected data is significantly improved.

It is still another advantage of the physiological data collection system of the present invention that by adjusting the quantity and placement of the electrodes of the disposable physiological sensor device or patch provides the capacity to use a multitude of industry recognized ECG algorithms and/or lead placement locations for testing purposes.

It is still another advantage of the physiological data collection system of the present invention that no patient identifiable information is contained within the data control module, affording complete privacy and protection to the patient for whom use is intended.

Various other features and advantages of the invention are disclosed and detailed in the following drawings, detailed description and claims.

DETAILED DESCRIPTION OF THE INVENTION

Before the invention is explained in full detail, it is to be understood that the invention is not limited in its application to the details of construction and the arrangement of components set forth in the following description or illustrated in the following drawings. The invention is capable of other embodiments and of being practiced or carried out in various ways. Also, it is to be understood that the phraseology and terminology used herein is for the purposes of description and should not be regarded as limiting. The use of "including" and "comprising" and variations thereof herein is meant to encompass the items listed thereafter and equivalents thereof as well as additional items.

Figure 2:
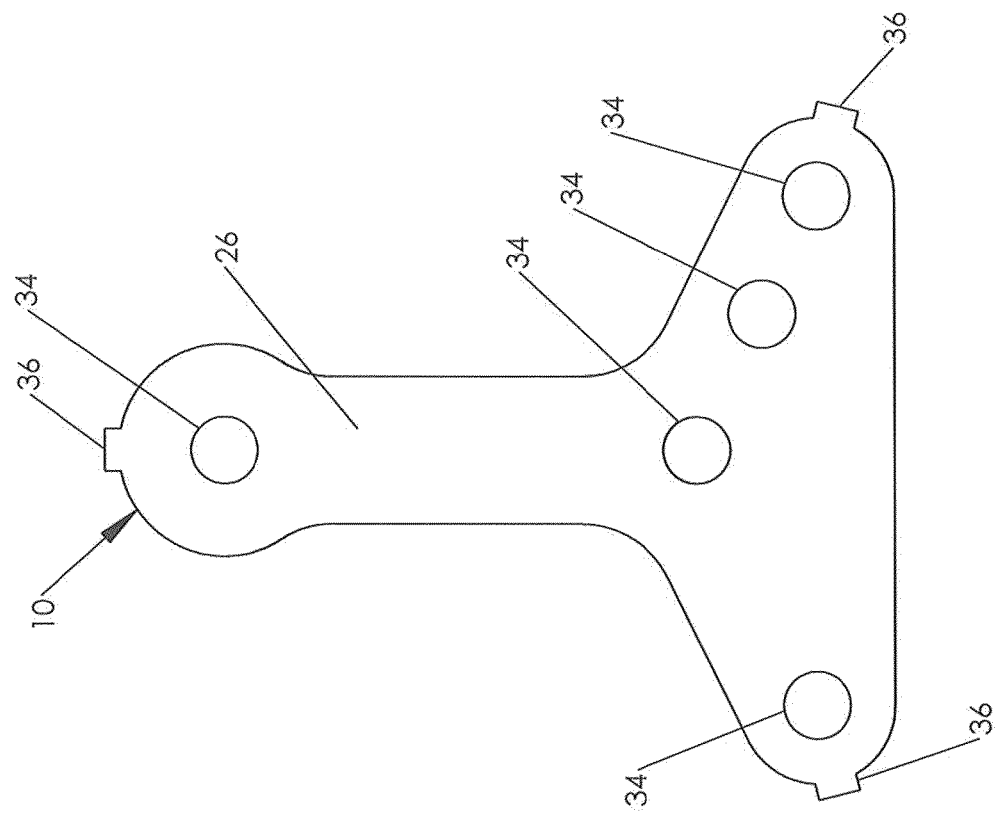
FIG. 2 is a rear view of the physiological sensor device or patch depicted in FIG. 1.
Figure 1:
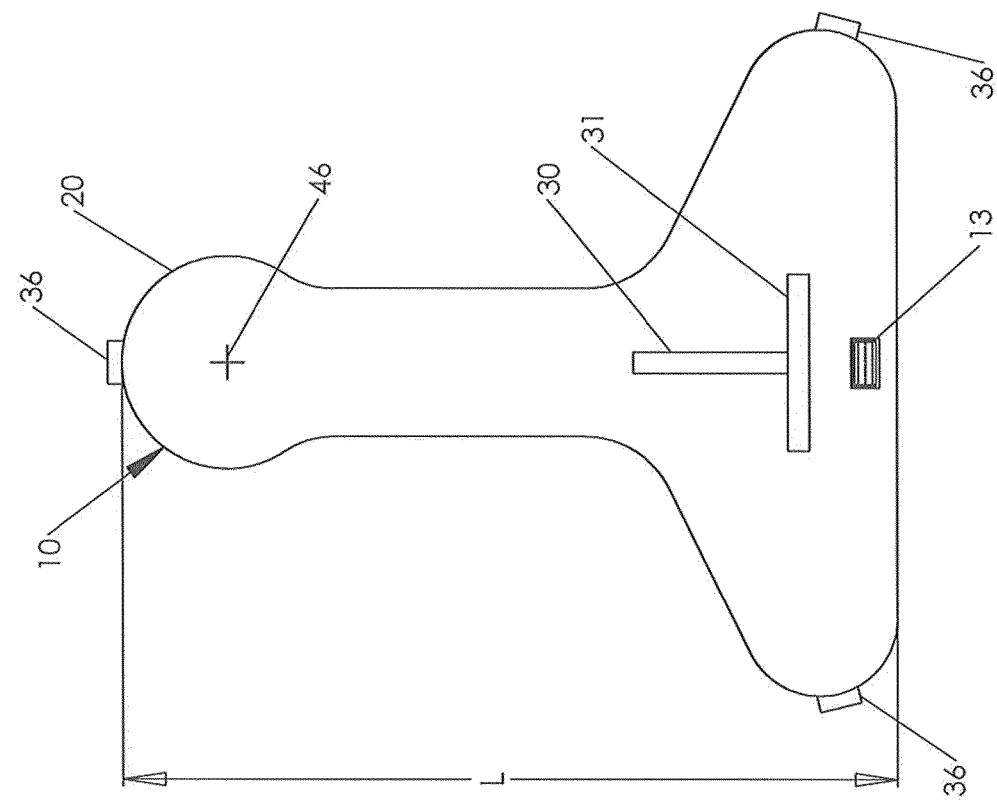
FIG. 1 is a front view of a physiological sensor device or patch according to one embodiment of the present invention.
Figure 3:
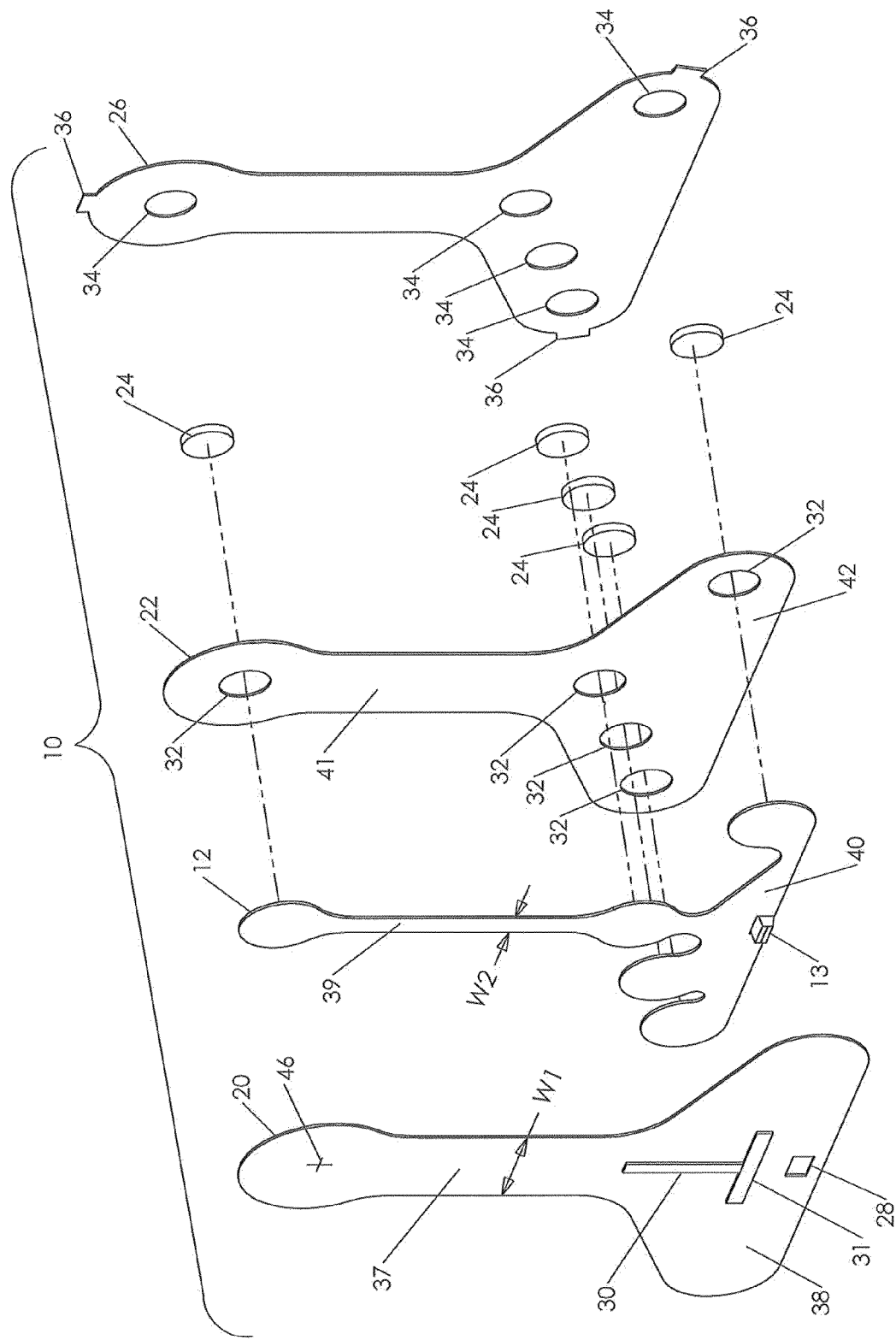
FIG. 3 is an exploded view of the physiological sensor device or patch of FIG. 1 viewed from the front.
Figure 4:
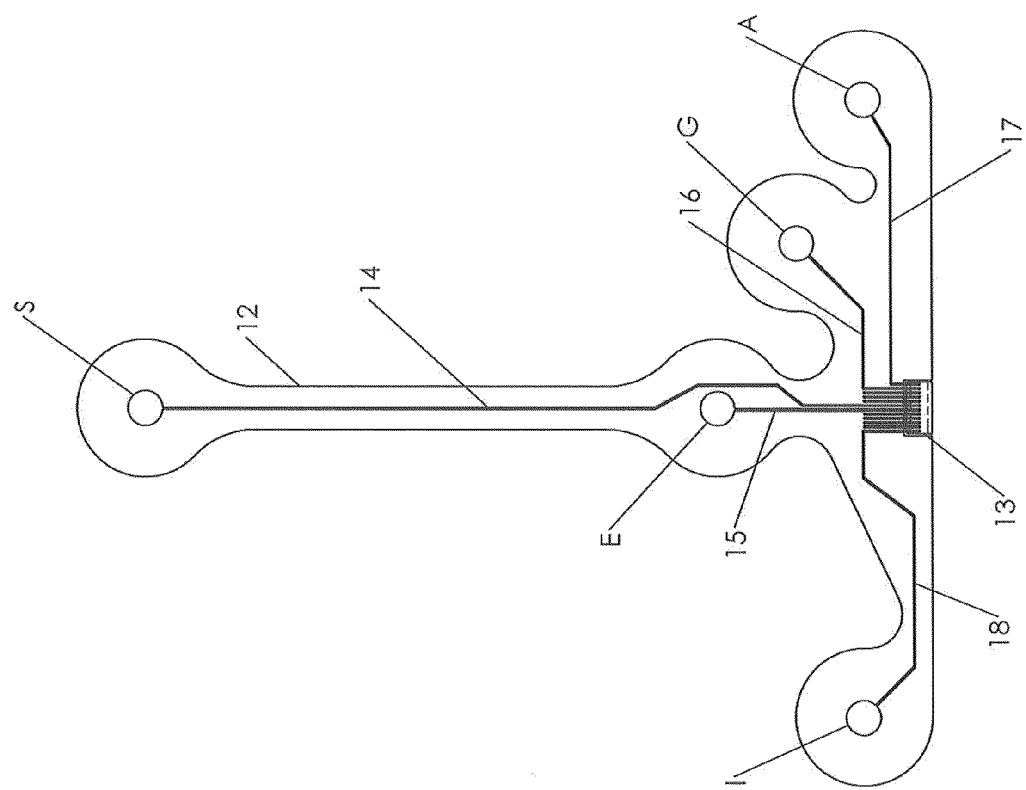
FIG. 4 is a rear view of a layer contained within the physiological sensor device or patch of FIG. 1 showing electronic components of the device.

Referring first to FIGS. 1-4 there is shown a physiological sensor device or patch 10 according to one embodiment of the present invention. FIG. 1 is a front view of the physiological sensor device or patch device 10. As used herein and in the claims the term "front" is understood to refer to a direction looking towards a side of the physiological sensor device or patch that is distal from, that is to say faces away from, the chest of a patient when the physiological sensor device or patch is attached to the patient in its' operative location. FIG. 2 is a rear view of the physiological sensor device or patch 10. As used herein and in the claims the term "rear" is understood to refer to a direction looking towards a side of the physiological sensor device or patch that is proximal to, that is to say faces towards, the chest of a patient when the physiological sensor device or patch is attached to the patient in its' operative location. As used herein and in the claims, the terms "top", "bottom", "above", "below", "higher", "lower" and similar terms indicative of vertical locations are understood to refer to a perspective looking towards a physiological sensor device or patch that is attached to a patient in its' operative location with the patient standing or sitting upright. FIG. 4 is a rear view of an intermediate circuit layer 12 contained within the physiological sensor device or patch 10. FIG. 3 is an exploded view of the physiological sensor device or patch 10.

As shown in FIG. 3 the physiological sensor device or patch 10 of this first embodiment comprises a plurality of layers including: a flexible outer front layer 20; a flexible intermediate circuit layer 12 having a plurality of electrodes and electrical conductors fixed to a back side of this intermediate layer; a third flexible layer 22 that is the back layer having an adhesive on a back side of it for adhering the physiological sensor device or patch 10 to the chest of a patient; a plurality of conductive gel pads 24 adhered to the flexible intermediate circuit layer 12 with each gel pad aligned with and in conductive communication with one of the electrodes A, E, I, S and G and protruding through a portal 32 in the third flexible layer 22; and a rearmost layer 26 that is a liner releasable from an adhesive on the on the back side of the third flexible layer 22. It is understood that as used herein and in the claims the term "plurality" means two or more.

Preferably, the flexible outer front layer 20 comprises a material that does not conduct electricity that is both breathable and stretchable while being water resistant, such as surgical grade foam. As illustrated in FIGS. 1 and 4 the flexible outer front layer 20 includes an outer surface that is distal from a patient when the physiological sensor device or patch 10 is in its' operative position fixed to the chest of a patient. The flexible outer front layer 20 has a portal 28 therein through which the single common connector 13 attached to the flexible intermediate circuit layer 12 protrudes. Preferably, a surface of the flexible outer front layer 20 that is distal from the chest of a patient when the physiological sensor device or patch 10 is attached to a patient in its' operative location is provided with markings 46 designed to aid the person applying the patch as to the correct alignment of the patch to anatomical landmarks on the body such as the manubrium. The flexible outer front layer 20 includes an inner surface which while not shown includes an adhesive that is used to attach the back side of the flexible outer front layer 20 to the front side of the flexible intermediate circuit layer 12. Preferably, a surface of flexible outer front layer 20 that is distal from the chest of a patient when the when the physiological sensor device or patch 10 is attached to a patient in its' operative location is provided with a means 30, 31 for fixing a data collection module to a front surface of the front layer of the physiological sensor device or patch. While the means 30, 31 may be any suitable means for attachment, including a suitable adhesive system, in a preferred embodiment a means for fixing a data collection module to the physiological sensor device or patch comprises a hook and loop fastening system. An example of a hook and loop fastening system is marketed under the trademark Velcro®. The hook tape presents a rough or hard side for mating with the loop tape that presents a soft or fuzzy side. The hook and loop tapes may be secured to the surface of flexible outer front layer 20 that is distal from the chest of a patient when the physiological sensor device or patch 10 is attached to a patient in its' operative location and the data collection module by an adhesive or any other suitable means. It is preferred that the loop component of the hook and loop fastening system is attached to the surface of flexible outer front layer 20 that is distal from the chest of a patient when the physiological sensor device or patch 10 is attached to a patient in its' operative location while the hook side of the fastening system would be attached to the outer rear surface of the data collection module. This configuration is preferable because depending on the chosen horizontal or vertical mounting position of the data collection module, a portion of the fastening system attached to the outer surface of the outer front layer may be left exposed. Preferably the means for fixing a data collection module to the physiological sensor device or patch has a vertical portion 30 and a horizontal portion 31. The functionality of this feature will be explained below with respect to a data collection module. However, in an instance where the common connector 13 is mated to a cable that extends to an EKG machine or other data collecting and processing device, the means for fastening 39, 31 may be utilized to secure the coupling cable (not shown) to the outer surface of the physiological sensor device or patch.

The flexible intermediate circuit layer 12 comprises a material that is non porous, and does not conduct electricity and is rigid enough to support the electrodes A, E, I, S, G and electrical conductors 14, 15, 16, 17, 18 and the common connector 13 that are attached to this layer. One material that may be used for fabricating the flexible intermediate layer 12 is a thin polyester film such as MYLAR®. The back side of the flexible intermediate circuit layer 12 to which the electrodes, electrical conductors and common connector are fixed is adhered to the front surface of the flexible layer 22 in a manner that does not interfere with the function of the electrodes, electrical conductors and common connector.

Each of the plurality of electrodes A, E, I, S is coupled to a substrate that is the flexible intermediate circuit layer 12. A single ground lead G is coupled to the substrate 12. It is understood that the ground lead G is in fact an electrode and in disclosing the invention it may be referred to herein as either an electrode or a ground lead. A plurality of electrical conductors 14, 15, 16, 17, 18 are coupled to the plurality of electrodes A, E, I, S, the ground lead G, the flexible intermediate circuit layer 12 and a single common connector 13. Each of the plurality of electrodes A, E, I, S, G is coupled to an individual conductor of the plurality of electrical conductors 14, 15, 16, 17, 18 on a one to one ratio. The electrodes and their associated individual coupled electrical conductors are arranged on the back side of the flexible intermediate circuit layer 12 such that distance between each conductor is sufficient to allow conductivity of electrical signals obtained by the electrodes to be transmitted in such a manner as to avoid interference or noise from the other electrodes and electrical conductors present on the circuit layer. They are also arranged in such a manner as to allow the signals from each individual electrode to be separately and individually identified at the common connector 13 where each conductor from the plurality of electrical conductors on the layer terminate. The electrodes and their coupled electrical conductors located on the rear surface of the flexible intermediate circuit layer 12 are comprised of a suitable material that allows the collection and transmission of the signals being collected from the skin of the patient in such a manner that noise and interference is eliminated. One such composition that is well known to be acceptable for both the construction of the electrodes and the electrical conductors is silver/silver chloride. After the electrodes and electrical conductors have been attached to the rear surface of the flexible intermediate circuit layer 12 a third flexible layer 22 is applied in such a manner that an adhesive on the front side of this third flexible layer covers the entire surface area of the back side of the flexible intermediate circuit layer 12 with the exception of the surface area occupied by the plurality of electrodes with the conductive gel pads 24 associated with the electrodes located in the portal 32 in the third flexible layer 22. The back surface of the third flexible layer 22 attaches to the front surface of the flexible liner layer 26. The flexible liner layer 26 is removed from the physiological sensor device or patch 10 before the physiological sensor device or patch is attached to a patient.

The third flexible layer 22 preferably comprises a material that does not conduct electricity and is both breathable and stretchable while being water resistant, such as a surgical grade foam. While not a requirement of construction, it is not unrealistic that both the flexible outer front layer 20 and the third flexible layer 22 are to be produced from like materials. The third flexible layer 22 is provided with a plurality of portals 32 that receive a plurality of conductive gel pads 24 which in the assembled physiological sensor device or patch are in conductive contact with the electrodes and ground lead A, E, I, S, G of the flexible intermediate circuit layer 12. Preferably each of the plurality of portals 32 that receive a plurality of conductive gel pads 24 is sized such that it is larger than the electrode with which it corresponds by the same diameter in any and all directions from the center position of the electrode. While not definitive, in the current embodiment of the invention, the outer edge of each of the plurality of portals 32 is five mm larger in any and all directions from the outer circumference of the electrode it surrounds.

Figure 11:
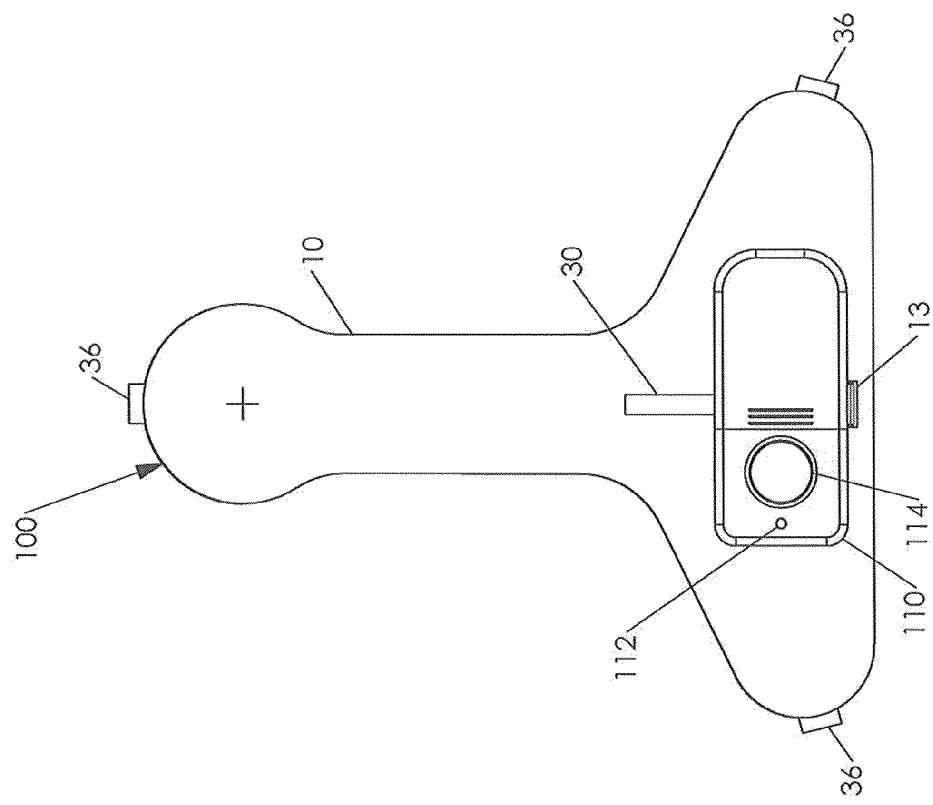
FIG. 11 is a front view of a system wherein the physiological sensor device or patch of the present invention is assembled with a data collection module mounted vertically thereon.
Figure 12:
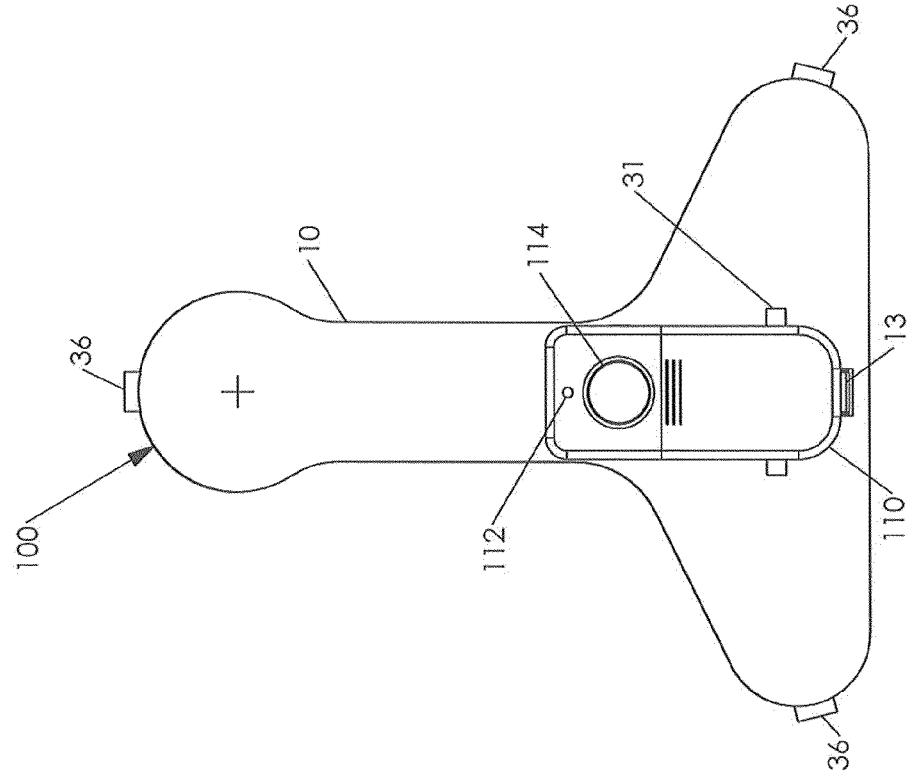
FIG. 12 is a front view of a system wherein a physiological sensor device or patch of the present invention is assembled with a data collection module mounted horizontally thereon.

The conductive gel pads 24 provide conductivity of the electrical signals that are collected at the skin of the patient to the electrodes A, E, I, S and the grounding electrode G located on the back side of the flexible intermediate circuit layer 12. In this embodiment, conductivity is obtained by means of a conductive gel, preferably a hydrogel electrolyte that enhances the conductive properties of the gel allowing a continuous contact for the signals to be transmitted from the surface of the patient's skin. The gel pads are constructed of foam pads made from a suitable material to hold the hydrogel such as reticulated foam that has been injected or saturated with the conductive hydrogel. The conductive gel pads 24 are in direct contact with the patient's skin at all times during the testing period. The signals collected at the surface of the patient's skin are conducted to the electrodes in conductive contact with the gel pads, then through the electrodes to the associated electrical conductors 14, 15, 17, 18 which conduct the signals to a single common connector 13. The common connector 13 includes a plurality of pins or sockets equal to at least the number of electrical conductors contained on the flexible intermediate circuit layer 12 of the physiological sensor device or patch 10. The common connector 13 extends through a portal 28 in the flexible outer front layer 20 and is located on a foldable tab to better accommodate the mating of the common connector 13 to a complementary connector of another device. Without limiting the connectivity of the physiological sensor device or patch to a data collection module, said connectivity may be made by means of a direct coupling of the physiological sensor device or patch to a conventional ECG monitor or by means of attaching a data control module 110 to the common connector 13, as shown in FIGS. 11 and 12.

Preferably, the shape of the third flexible layer 22 is an exact duplicate of the shape and outer measurements to the flexible outer front layer 20 of the physiological sensor device or patch 10. A rear surface of the third flexible layer 22 is coated with an adhesive over the entire surface area with the exception of the portals 32 that receive the conductive gel pads 24. The adhesive is a hypoallergenic adhesive having properties that allow the rear surface of the third flexible layer 22 to be attached directly to the surface of a patient's skin at the proper location to allow collection of the desired physiological data from the patient's body. The bonding properties of the adhesive should be sufficient in strength to allow the physiological sensor device or patch 10 to be worn by a patient for twenty four to forty eight hours prior to any significant loss of attachment to the skin.

The rearmost layer 26 of the physiological sensor device 10 or patch is a releasable liner layer. The releasable liner layer protects the adhesive contained on the rear surface of the third flexible layer 22 and the plurality of conductive gel pads 24 from exposure to the environment or contamination until such time as the physiological sensor device or patch is to be attached to a patient. The releasable liner layer is preferably constructed of a wax-covered paper material that allows its' outer surface to be attached to the rear surface of the third flexible layer 22. The wax coated surface of the releasable liner layer does not impede the adhesive properties of the adhesive that has been applied to rear surface of the third flexible layer. The releasable liner layer 26 is provided with a plurality of raised portions 34 that are equal in quantity and complementary to the locations of the plurality of conductive gel pads 24 so that the raised portions overlie the conductive gel pads to protect the conductive gel pads. While the raised portions 34 of the releasable liner layer are a preferable feature, it is understood that they may be omitted if the conductive gel pads are protected by another means of protection. The releasable liner layer is provided with at least one tab 36 that extends from an outer edge of the releasable liner layer to aid in removal of the releasable liner layer before applying the physiological sensor device 10 or patch to a patient. The releasable liner layer may or may not be provided with perforations or multiple segments to allow the removal of the releasable liner layer in sections to allow for easier alignment and attachment to the patient.

If desired for any of the embodiments disclosed herein, the adhesive may be omitted from the back side of the third flexible layer 22, and instead a suitable adhesive may be applied to the skin of a patient in the appropriate area. The physiological sensor device or patch is then placed onto the patient and secured to the patient by the separately applied adhesive. In this alternative embodiment the physiological sensor device or patch comprises the flexible outer front layer 20, the third flexible layer 22, and the flexible intermediate circuit layer 12 and conductive gel pads 24 as described above. If desired each of the conductive gel pads may be protected by a removable protective layer. The physiological sensor device or patch may be packaged in a suitable material, and removed for placement when the adhesive is separately applied to the chest of a patient.

While desired placement locations on the chest for electrodes are the same for both male and female patients, the physical differences attributed to breast size are a known issue that is currently unresolved by prior art. In order for the electrodes to be properly positioned and properly attached to a patient's chest, the physiological sensor device or patch 10 must be designed for the anatomy of the patient for which its use is intended. The physiological sensor device or patch 10 of the present invention is not gender specific in that it may be used on both male and female patients with no discernable difference in the physiological data being collected. Generally speaking, each layer of the physiological sensor device has, when attached to a standing person's chest, a vertically extending portion with a horizontally extending portion located at a lower end of the vertically extending portion and extending from both sides of the vertically extending portion such that the physiological sensor device or patch 10 of the first embodiment has the shape or appearance of an inverted T. In FIG. 3 with respect to the flexible outer front layer 20 is provided on the vertically extending portion 37 of the inverted T with markings 46 designed to aid the person applying the patch as to the correct alignment of the patch to anatomical landmarks on the body such as the manubrium. Inasmuch as the mean length of a male sternum is twenty-two mm longer than that of females, and the mean width at the fourth rib location of females is nine mm narrower than that of males, keeping the width W1 of the vertically extending portion 37 of the inverted T where it overlies the sternum to no more than forty mm and the length to no more than one hundred and seventy mm allows the same physiological sensor device or patch 10 to be applied to either a male or a female in eighty-five percent of all adult patients. It is understood that alternative embodiments of the physiological sensor device or patch comprising a width W1 greater than forty mm and/or the length L as depicted in FIG. 1 being greater than one hundred and seventy mm while not shown, are anticipated to facilitate the use of the physiological sensor device or patch 10 on patients who are of a larger stature than the average person and or obese in that use of the preferred embodiment of the physiological sensor device or patch would not provide suitable test results.

The physiological sensor device or patch 10 of the present invention is designed such that the top of the vertically extending portion 37 of the inverted T is placed just below the suprasternal notch (aka jugular notch) or clavicle at the top of the manubruim allowing for the proper placement of electrode S on the sternal manubrium. The vertically extending portion 37 of the inverted T then extends downward overlying the sternum. The length L of the physiological sensor device or patch 10 is sufficient to accommodate placement of the E electrode at the lower portion of the xiphoid process. At the lower end of vertically extending portion 37 of the inverted T the horizontally portion 38 of the inverted T of the physiological sensor device or patch 10 the horizontal portion 38 of the inverted T extends left and right substantially equal distances to overlie the sixth and seventh true ribs to allow the proper placement of the A and I electrodes. While the common or grounding electrode G can be placed at any location on the physiological sensor device or patch in this first embodiment it is located substantially midway between the E and I electrodes. It is understood that the flexible intermediate circuit layer 12 also has the general shape of an inverted T with a vertically extending portion 39 and a horizontally extending portion 40, and that the third flexible layer 22 also has the general shape of an inverted T with a vertically extending portion 41 and a horizontally extending portion 42.

In this first embodiment a further feature that enhances the use of the physiological sensor device or patch 10 for a female patient is that the width W2 of the vertical portion 39 of the flexible intermediate circuit layer 12 is substantially less than the width W1 of the flexible outer front layer 20 and the identically sized third flexible layer 22. Inasmuch as the flexible intermediate circuit layer 12 comprises a stiffer material, such as Mylar, while the flexible outer front layer 20 and the third flexible layer 22 comprise a less stiff material, such as surgical grade foam, the vertical portion of the physiological sensor device or patch can bend to adapt to the contours of the chest of a female patient between her breasts. This should enhance the comfort of the physiological sensor device or patch for a female patient.

Put another way, there is provided in accordance with the present invention a unisex physiological sensor device or patch 10 having the shape or appearance of an inverted T wherein the width W1 of the vertically extending portion 37 of the inverted T is small enough to overlie the sternum and be accommodated between the breasts of a female and the horizontally extending portion 38 of the inverted T is located below the breasts of a female.

In this first embodiment the plurality of electrodes A, E, I, S and the ground lead G are disposed to provide the placement of five electrodes for acquiring standard five-electrode, twelve lead ECG data when the EASI ECG algorithm is applied. The plurality of electrodes are positioned within the physiological sensor device, sometimes referred to in the art as a patch, in a sensor array such that when the physiological sensor device or patch is accurately positioned and properly attached to a patient's chest, the plurality of electrodes acquire standard five-electrode, twelve lead ECG data when the EASI ECG algorithm is applied. When accurate placement location and proper attachment position are obtained, the electrodes sense electrical potentials generated by a patient's body. This embodiment provides more accurate serial comparisons over time, being less susceptible to noise and interference over bulky ten electrode twelve-lead systems while allowing continuous twelve lead monitoring typically only found in two-lead II and V1 based 5 electrode systems.

While not shown in the drawings, the physiological sensor device or patch 10 of the invention is packaged in a hermetically sealed, easy to open, disposable pouch or packaging vessel that contains a physiological sensor device or patch until such time as it is to be attached to the patient. Included in the packaging are detailed instructions and or diagrams to aid in the determination of proper alignment and position on a patient to ensure accurate data collection. Additionally, a disposable wipe or pad containing a cleansing solution to prep the area of the skin for attachment of the physiological sensor device or patch may also be included.

A physiological sensor device or patch of any embodiment of the present invention is designed to be attached to the surface skin of the patient's chest either by the patient without assistance from another person, or by another person who may be assisting the patient. The patient or the assisting individual removes the physiological sensor device or patch 10 from its packaging and while following the included detailed instructions/diagrams, preps the desired placement area in the proper manner. After a proper prep has been completed, the releasable liner layer 26 or a portion thereof is removed. Thereafter utilizing the markings 46 on the front of the flexible outer front layer 20 the person applying the physiological sensor device or patch 10 applies it at the proper location of the patient. The person applying the physiological sensor device or patch then, if necessary, removes the remaining areas of the releasable liner layer 26 and applies pressure by hand to the entire front surface of the flexible outer front layer 20 to assure adhesion to the skin of the patient over the entire surface area of the physiological sensor device or patch. It should be understood that the preparation and attachment to the skin of a patient is purposely designed and intended to be performed by a person who does not have to be skilled or trained by the medical community.

A physiological sensor device or patch of any embodiment of the present invention is designed to be a single use disposable device that is worn by the patient on a continuous basis for a period of time of twenty four to no more than forty eight hours.

Either before or after attachment of the physiological sensor device or patch to a patient is complete, a data control module 110, which will be described below, or a cable coupling the physiological sensor device or patch directly to a monitoring device, such as an EKG machine, is coupled to the physiological sensor device or patch 10 via the common connector 13. After a patient's physiological data has been successfully collected, the data collection module 110 or the direct coupling cable is separated from the common connector 13. The patient or assisting person then removes the physiological sensor device or patch from the surface of the patient's body. If adhesion of the physiological sensor device or patch to the patient at the time of removal is such that there is discomfort to the patient, or difficulty of removal is experienced, the patient may gain assistance in removal by applying warm or hot water to the physiological sensor device or patch and adjacent areas. The suggested method would be to have the patient enter a shower and place himself/herself under a steady stream of warm/hot water to assist in breaking the adhesive bond of the physiological sensor device or patch with the skin of the patient.

Figure 5:
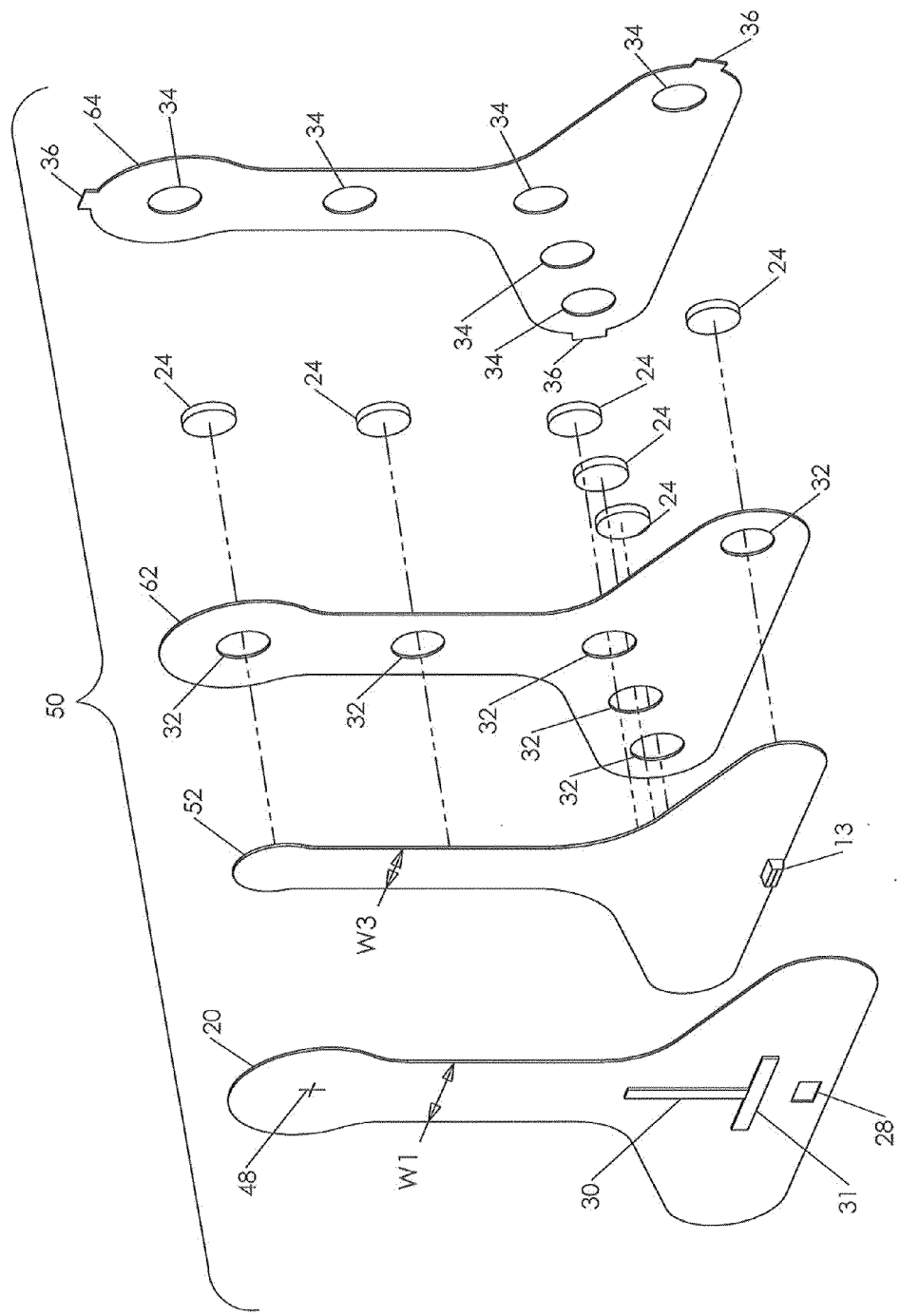
FIG. 5 is an exploded view of an alternative embodiment of a physiological sensor device or patch according to the present invention viewed from the front.
Figure 6:
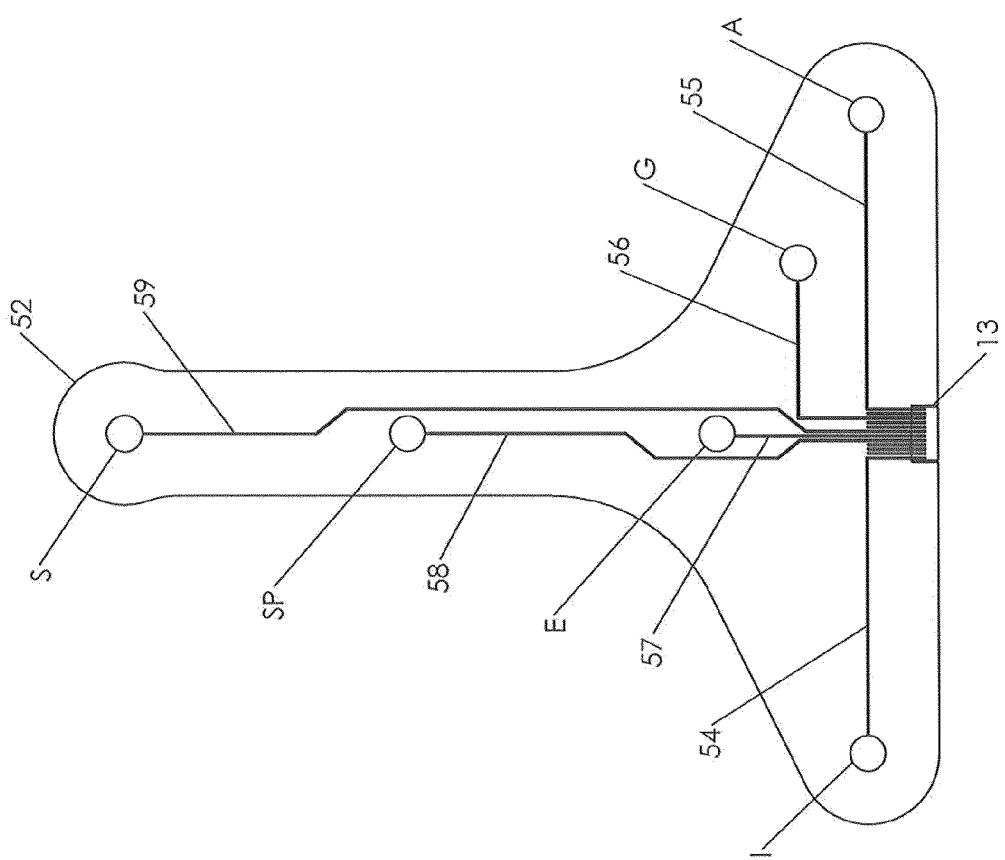
FIG. 6 is a rear view of a layer contained within the physiological sensor device or patch of FIG. 7 showing electronic components of the device.

An alternative embodiment of a physiological sensor device or patch 50 of the present invention is shown in FIGS. 5 and 6. FIG. 5 is an exploded view of the alternative embodiment viewed from the front, and FIG. 6 is a rear view of the flexible intermediate circuit layer 52 of this embodiment. This alternative embodiment is like the embodiment of FIGS. 1 to 4 with two notable distinctions, namely an additional spare electrode SP and the width W3 of the vertical portion of the flexible intermediate circuit layer 52.

A flexible outer front layer 20 of this embodiment is the same as the flexible outer front layer 20 of the first embodiment including: markings 48 designed to aid the person applying the patch; means 30, 31 for fixing a data collection module to the physiological sensor device or patch; and a portal 28 for receiving the single common connector 13. The flexible intermediate circuit layer 52 of this embodiment includes electrodes A, E, I, S, SP and a ground lead G which are in circuit communication with a common connector 13 via electrical conductors 54, 55, 56, 57, 58 and 59. Electrode SP is a spare electrode located such that when the physiological sensor device or patch 50 is applied to the chest of a patient the spare electrode SP is located substantially midway along the length of the patient's sternum at an equal distance between the S and E electrodes. The spare electrode SP may be used to facilitate the collection of additional physiological data from the patient such as body temperature or respiration. In this embodiment the width W3 of the vertically extending portion of the flexible intermediate layer 52 is substantially the same as the width W1 of the vertically extending portion of the flexible outer front layer 20. It is understood that the width W3 of the vertically extending portion of an assembled physiological sensor device or patch 50 of this embodiment may be made smaller than the width W1 of the flexible outer front layer 20 and the third flexible layer 22 of the first embodiment to better fit between the breasts of a female patient to compensate for being somewhat less flexible than the structure of the vertically extending portion of the physiological sensor device or patch 10 of the first embodiment as described above. The third flexible layer 62 is substantially the same as the third flexible layer 22 of the first embodiment, but it includes an additional portal 32 to accommodate an additional conductive gel pad 24 that is associated with the spare electrode SP. The rearmost layer 64 that is a removable liner is substantially the same as the rearmost layer 26 of the first embodiment, but it includes an additional raised portion 34 to accommodate the additional conductive gel pad 24 that is associated with the spare electrode SP.

It is understood that features of the first embodiment and this second embodiment relating to the width of the flexible intermediate circuit layers 12, 52 and the presence or absence of a spare electrode SP may be employed in any combination desired without varying from the scope of the invention.

Figure 8:
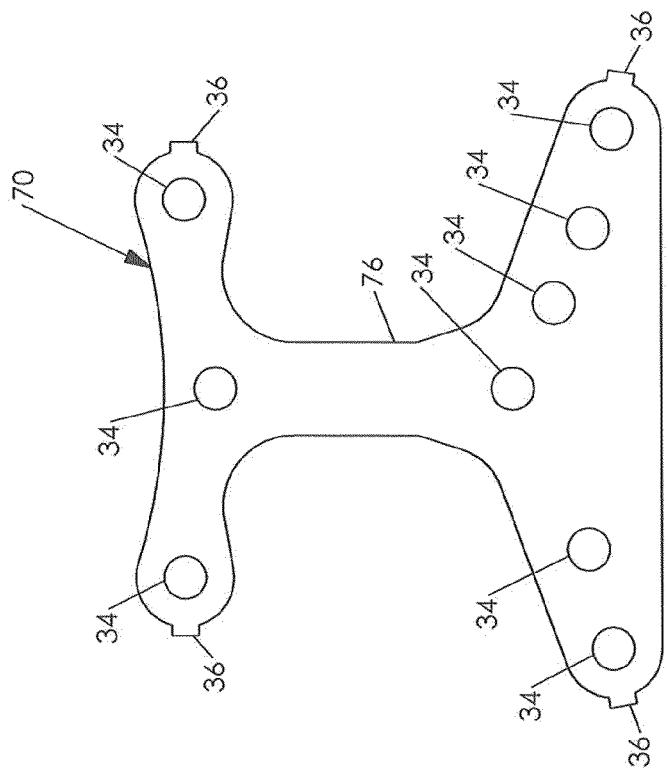
FIG. 8 is a rear view of the physiological sensor device or patch depicted in FIG. 7.
Figure 7:
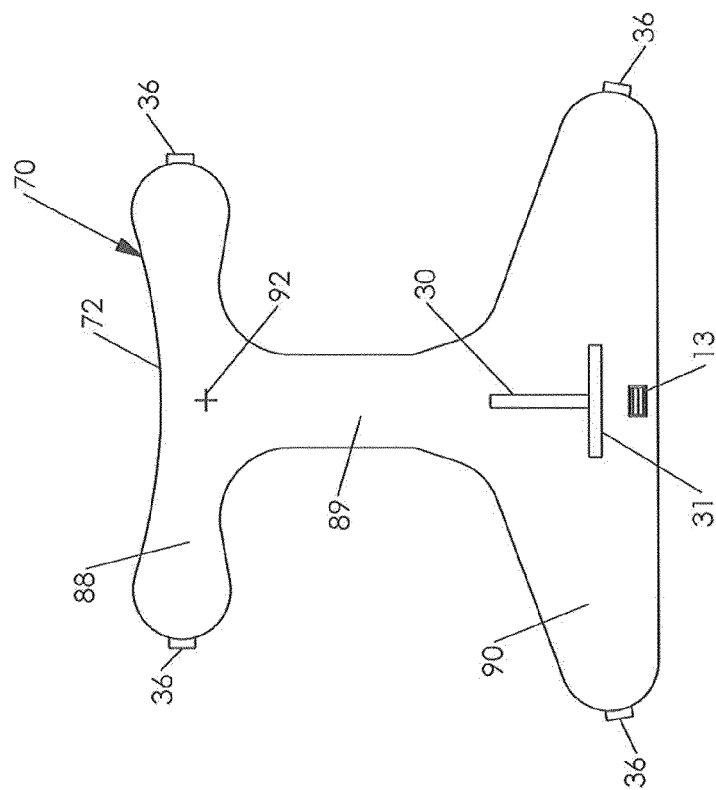
FIG. 7 is a front view of another alternative embodiment of a physiological sensor device or patch according to the present invention.
Figure 9:
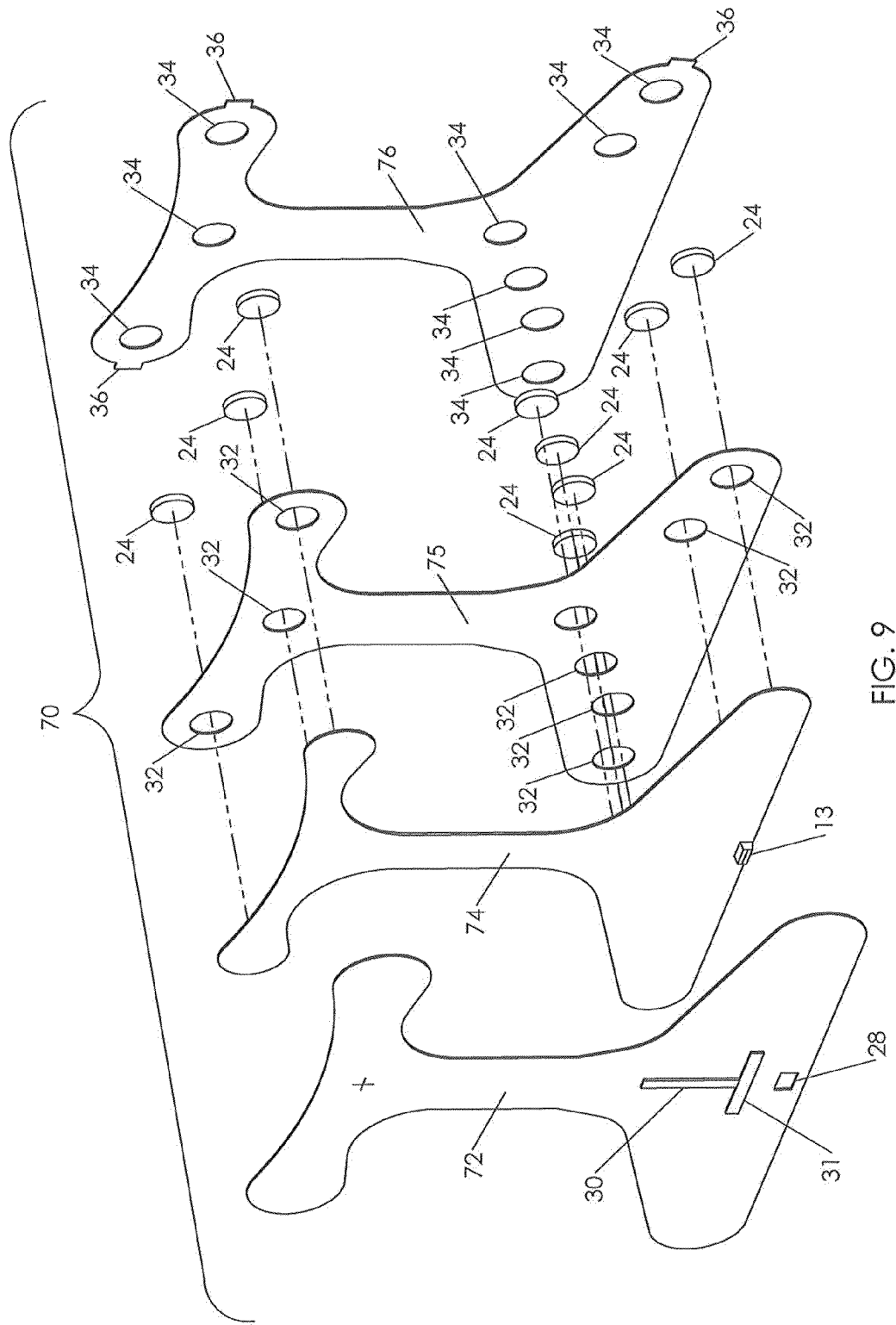
FIG. 9 is an exploded view of the physiological sensor device or patch of FIG. 7 viewed from the front.
Figure 10:
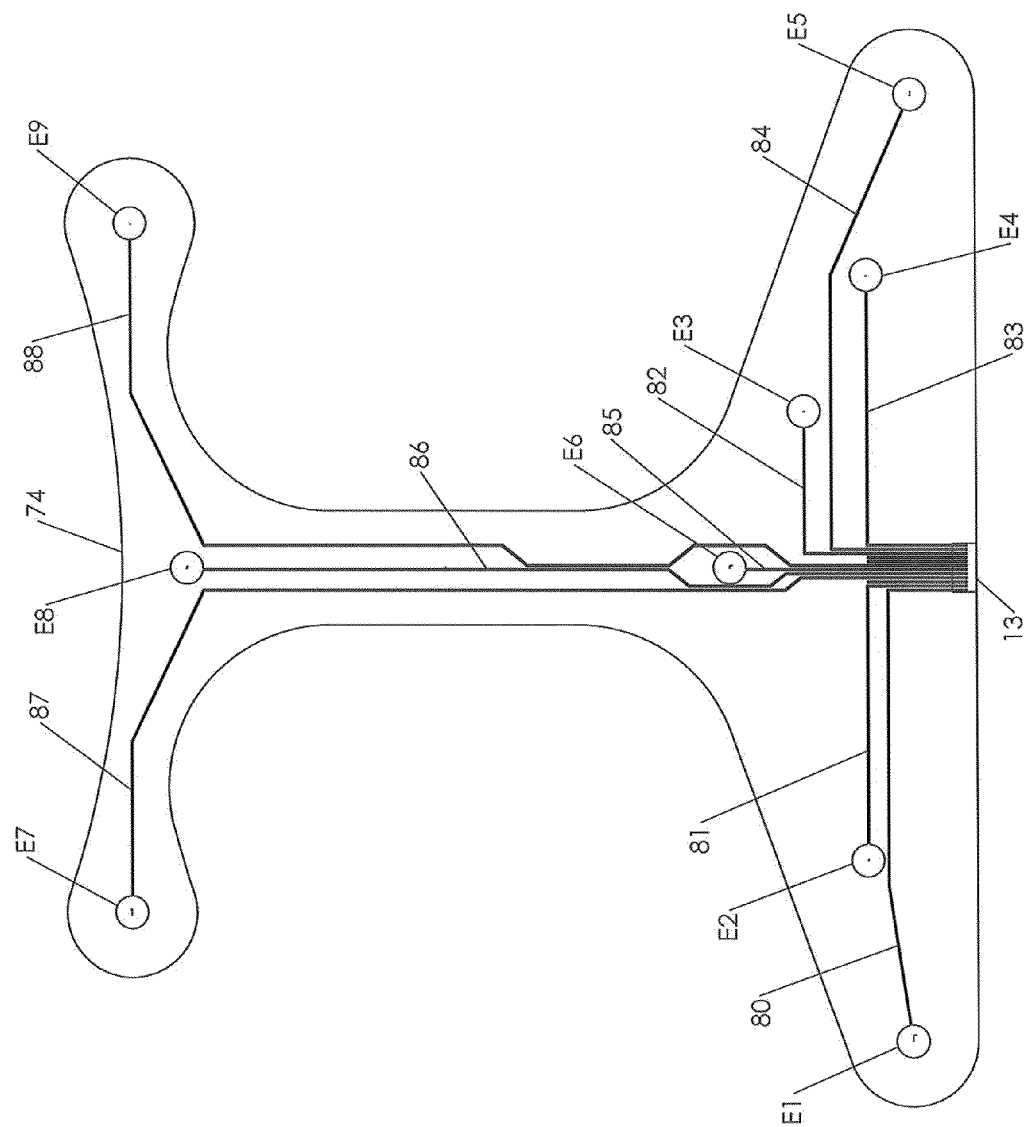
FIG. 10 is a rear view of a layer contained within the physiological sensor device or patch of FIG. 7 showing electronic components of the device.

Another alternative embodiment of a physiological sensor device or patch 70 of the present invention is shown in FIGS. 7, 8, 9 and 10. FIG. 7 is a front view of this alternative embodiment; FIG. 8 is a rear view of this alternative embodiment; FIG. 9 is an exploded view of this alternative embodiment viewed from the front; and FIG. 10 is a rear view the flexible intermediate circuit layer 74 of this embodiment. This alternative embodiment is like the embodiment of FIGS. 5 and 6 with two notable distinctions, namely an additional horizontally extending portion 88 located at the top of the vertically extending portion 89 opposite the horizontally extending portion 90 at the lower end of the vertically extending portion that is present in the previously described embodiments, and a larger number of electrodes that provide added versatility to the use of the physiological sensor device or patch 70. The configuration of this embodiment is such that it still allows the use of the physiological sensor device or patch on either a male or a female patient as the previously disclosed embodiments do.

A flexible outer front layer 72 of this embodiment is the same as the flexible outer front layer 20 of the first embodiment and second embodiments described above including: markings 92 designed to aid the person applying the patch; means 30, 31 for fixing a data collection device to the physiological sensor device or patch; and a portal 28 for receiving the single common connector 13. The placement alignment markers as illustrated by 46 on FIG. 1, 48 on FIGS. 5 and 92 on FIG. 7 are all in the same location on the front surface of the flexible outer front layer to insure proper placement on the skin of a patient in the same location regardless of the embodiment being used to facilitate the acquisition of accurate and complete physiological data from the patient being tested.

The flexible intermediate circuit layer 74 of this embodiment includes electrodes E1, E2, E3, E4, E5, E6, E7, E8 and E9 which are in circuit communication with a common connector 13 via electrical conductors 80, 81, 82, 83, 84, 85, 86, 87 and 89. While FIGS. 4 and 6 depict electrode locations for analysis and interpretation utilizing the EASI algorithm, the electrode locations as depicted in FIG. 10 allow for the collection of physiological data from the patient for analysis and interpretation by both the MEANS and EASI algorithms. More specifically, EASI requires use of the electrodes E, A, S and I of FIGS. 4 and 6, which correlate to electrode array in FIG. 10 such that E is E6, A is E4, I is E2 and S is E8. For the MEANS algorithm, the electrodes utilized would be E1, E5, E7 and E9 while E3 would be common ground for both algorithms. The electrode array of a physiological sensor device or patch 70 of this alternative embodiment is capable of acquiring physiological data from a patient that may be analyzed and interpreted by multiple algorithms while only requiring the patient to undergo a single test. The benefit of this embodiment is that the patient is tested for the same 24 to 48 hour time period as each individual test would require, resulting in a time savings of the 24 to 48 hours that the second test would have required. The patient is not inconvenienced, test results are obtained more rapidly and a comparison is able to be made against both resulting reports in a more accurate manner in that testing conditions were exactly the same for each.

It is understood that the flexible intermediate circuit layer 74 of this third embodiment may if desired include a spare electrode like the spare electrode SP of the second embodiment located such that when the physiological sensor device or patch 70 is applied to the chest of a patient the spare electrode is located substantially midway along the length of the patient's sternum at an equal distance between electrodes E6 and E8. A conductor connects the spare electrode to the single common connector 13. As described above with respect to the second embodiment the spare electrode may be used to facilitate the collection of additional data from the patient such as an additional electrode to collect physiological data, temperature sensor, or change in resistance to measure breathing or chest compressions.

The third flexible layer 75 is substantially the same as the third flexible layers 22, 62 of the first and second embodiments described above, but it includes additional portals 32 to accommodate the additional conductive gel pads 24 that are associated with the larger number of electrodes in this embodiment. The rearmost layer 76 that is a removable liner is substantially the same as the rearmost layers 26, 64 of the first and second embodiments described above, but it includes additional of raised portions 34 to accommodate the additional conductive gel pads 24 that are associated with the larger number of electrodes in this embodiment.

It is understood that features of the first embodiment relating to the relative width of the vertically extending portion flexible intermediate circuit layer may be employed in this embodiment to enhance the use of this embodiment for female patients.

Referring now to FIG. 11 there is shown a front view of a physiological data collection system 100 wherein a physiological sensor device or patch 10 of the present invention is assembled with a data collection module 110 mounted vertically on the flexible outer front layer of the physiological sensor device or patch. FIG. 12 is a front view of the system wherein the physiological sensor device or patch 10 is assembled with a data collection module 110 that is mounted horizontally on the physiological sensor device or patch. It is understood that the orientation of the data collection module on the flexible outer front layer of the physiological sensor device or patch, be it horizontal or vertical has no effect on the manner in which the invention operates. The choice of horizontal or vertical orientation of the data collection module is purely for the purposes of patient comfort and concealment of the physiological data collection system during the testing period.

As described above the front surface of the flexible outer front layer is provided with a means 30, 31 for fixing the data collection module 110 thereto. While the means 30, 31 may be any suitable means for attachment, including a suitable adhesive system, a preferred means for fixing a data collection module to the physiological sensor device or patch comprises a hook and loop fastening system as described above secured to a surface of flexible outer front layer that is distal from the chest of a patient when the physiological sensor device or patch is attached to a patient in its operative location. Preferably the means for fixing a data collection module to the physiological sensor device or patch has a vertical portion 30 and a horizontal portion 31. It is preferred that the loop side of the hook and loop fastening system is attached to the surface of flexible outer front layer. This configuration is preferable because depending on the chosen horizontal or vertical orientation of the data collection module, a portion of the fastening system may be left exposed and this orientation will avoid having the hook portion attaching itself to a patient's clothing that overlies the physiological data collection system.

Figure 14:
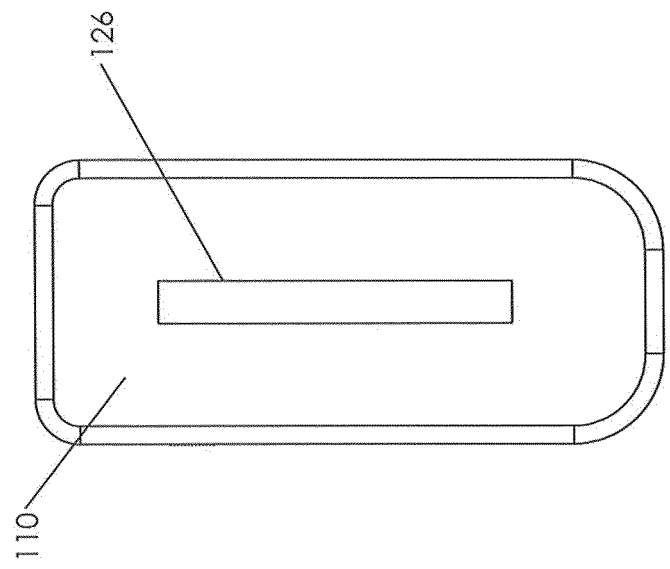
FIG. 14 is a bottom view of the data collection module of FIG. 13.
Figure 13:
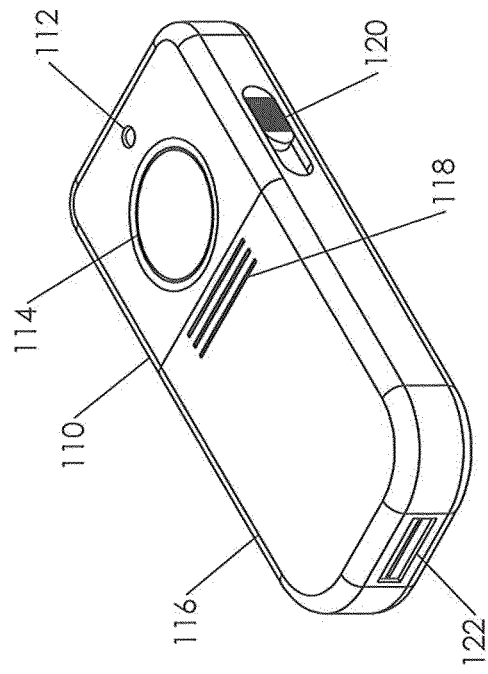
FIG. 13 is a perspective view of a first embodiment of a data collection module.
Figure 15:
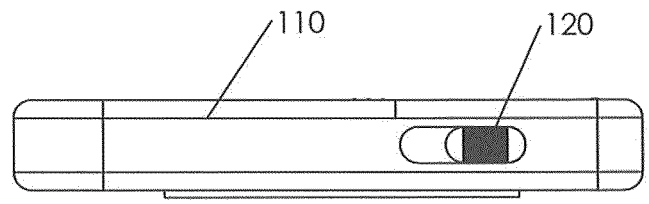
FIG. 15 is a view of a first long side of the data collection module of FIG. 13.
Figure 16:
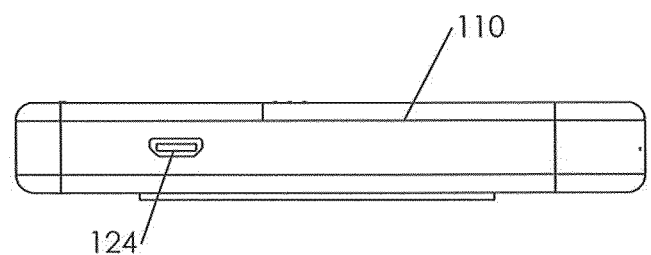
FIG. 16 is a view of a second long side of the data collection module of FIG. 13.
Figure 17:
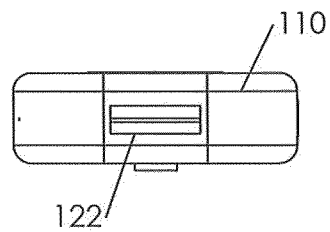
FIG. 17 is a view of a first short side of the data collection module of FIG. 13.
Figure 18:
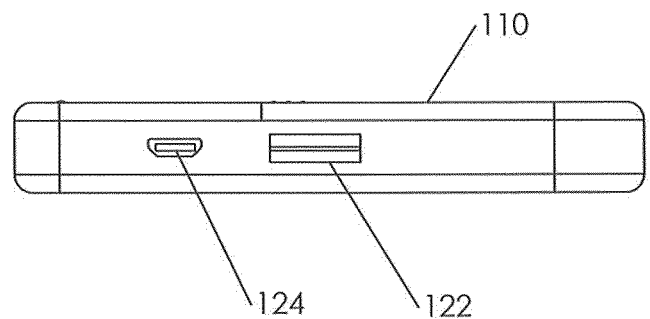
FIG. 18 is a view of a first long side of a second embodiment of a data collection module of FIG. 13.
Figure 19:
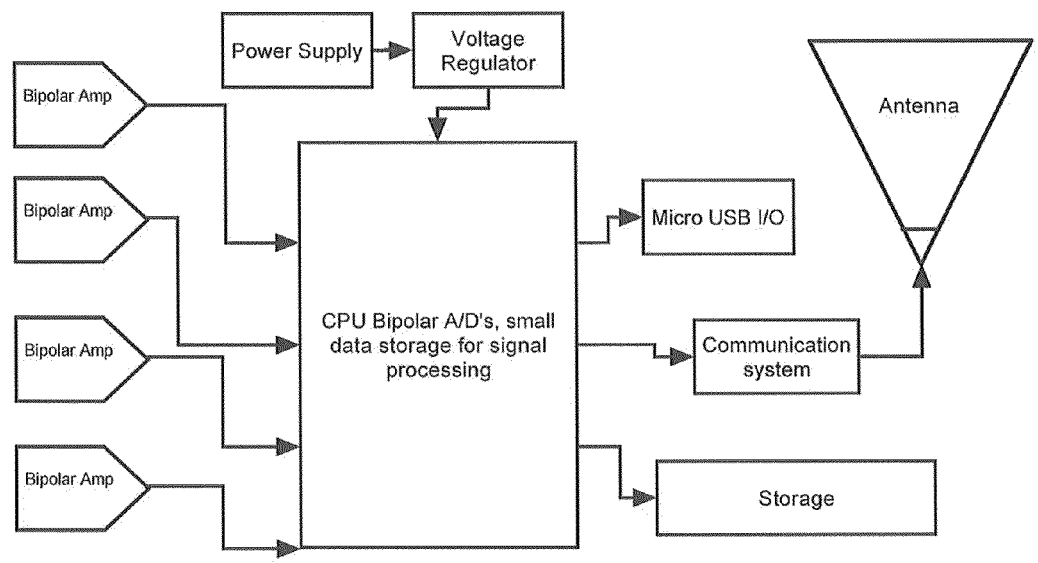
FIG. 19 is a schematic representation of the electronic components of a data collection module.

The structure and function of an exemplary data collection module 110 will be disclosed with reference to FIGS. 13 to 19. FIG. 13 is a perspective view of a first embodiment of a data collection module; FIG. 14 is a bottom view of the data collection module; FIG. 15 is a view of a first long side of the data collection module; FIG. 16 is a view of a second long side of the data collection module; FIG. 17 is a view of a first short side of the data collection module; FIG. 18 is a view of a first long side of a second embodiment of a data collection module; and FIG. 19 is a schematic representation of the electronic components of a data collection module.

The following description is based on the placement of the data collection module 110 upon the outer surface of the physiological sensor device or patch in such a manner that when worn by the patient, the long sides of the data collection module 110 are oriented vertically with respect to the patient in such that the recessed on/off switch 120 of the data collection module shown in FIG. 15 is located on the right side of the patient with the micro USB port 124 of the data collection module shown in FIG. 16 located on the left side of the patient and the data collection port 122 shown in FIG. 17 of the data collection module is located at or near the bottom of the patient's sternum.

The data collection module 110 of FIG. 13 has a housing constructed of a solid material that is both light weight and provides high tensile strength to protect the contents of the housing. One such material is ABS Plastic. In a preferred embodiment the overall width of the data collection module 110 should be no wider than a vertically extending portion of the physiological sensor device or patch. The length of the data collection module should be no longer than the distance from the base of the data collection port 13 of the physiological sensor device or patch to the point equal to the height of the upper most electrode contained within the physiological sensor device or patch shown in FIGS. 1 to 4. The overall thickness of the housing shall be such that it contains the necessary components within the housing when attached to the physiological sensor device or patch 10 as shown in FIG. 1 in a manner that the overall thickness of both the data collection module and the physiological sensor device or patch are virtually undetectable or unnoticeable when placed on the skin of the patient during the testing period, allowing the patient to conduct his or her normal daily activities while the test is performed.

The outer surface of the data collection module 110 includes a multicolor LED 112 and an event button 114. The multicolor LED can give an indication of the status of the data collection module, for example a green illumination may indicate powered on and functioning and while red may indicate low battery, and blue may indicate a wireless transmission is in progress. The event button should be disposed recessed with respect to an outer surface of the data collection module to prevent unintentional activation of an event recording process. When and if a patient who is undergoing a test experiences feelings or symptoms of a cardiac event, the patient causes the data collection module to record the "event" by pressing the event button. At such time the collected physiological data preceding the "event" by a predetermined length of time and the data collected during a predetermined length of time following the "event" are segregated and marked with a time stamp. If desired an "event" can trigger a visual indication of the "event" via the multicolor LED 112 and/or an audible alert sounded to confirm the initiation of an "event". If the data collection module is equipped with a wireless transmitter the collected data relating to the "event" is then transmitted to the remote monitoring and analysis center for immediate analysis and interpretation. If the interpretation signals a cause for concern, the patient is then contacted and given appropriate instructions by a qualified technician from the remote monitoring and analysis center.

The data collection module 110 further includes a removable cover 116 which may be level with or recessed with respect to an outer surface of the data collection module. In another embodiment of the data collection module described below a data collection module may include a multiline LCD display. Additionally, the outer surface of the invention may be provided with the name of the provider and a contact phone number for the provider in such a manner as to not be removable or easily worn off. Preferably one of the long sides of the data collection module includes an on/off switch 120 as shown on FIG. 15, which is recessed below the outer surface of the data collection module in such a manner as to prevent the accidental powering off of the data collection module during the testing period.

Preferably one of the long sides of the data collection module includes a micro USB port 124 as shown in FIG. 16. The micro USB port should be flush with the exterior surface of the data collection module and may used to provide power to the data collection module and the ability to program or communicate with the data collection module should wireless communications not be available.

In the preferred embodiment of the data collection module 110 the data collection port 122 shown in FIG. 18 should be flush with the outer surface of the data collection module and have a shape configured to couple with the common connector 13 of the physiological sensor device or patch. It is understood that a single data collection module may have data collection ports 122 located on both a short side of the data collection module as shown in FIG. 17 and a long side of the data collection module as shown in FIG. 18 with the amplifiers and the central processing unit processing the physiological data from the data collection port that is in use. It is understood that while FIG. 18 shows the amplifiers as bipolar amplifiers, that any suitable type of amplifiers including for example programmable gain amplifiers may be used in the practice of this invention. This configuration allows a single data collection module to be oriented either vertically or horizontally with respect to the physiological sensor device or patch. Preferably the data collection port 122 of the data collection module shall be "female" while common connector 13 of the physiological sensor device or patch shall be "male" such that the when coupled together they allow the continuation of transmission of physiological data from the physiological sensor device or patch to the data collection module in a continuous and uninterrupted manner. This connection shall not allow for any movement or play within the ports such that a creation of noise or signal loss would occur.

Preferably the data collection module 110 of FIG. 13 includes a removable cover 116 provided with raised ridges 118 to facilitate removal of the cover. The data collection module contains at a minimum a rechargeable/reusable power source and a printed circuit board, which is shown schematically in FIG. 19. In the preferred embodiment of the data collection module the rechargeable/reusable power source (not shown) is a self contained unit constructed from a known material that is both reusable and rechargeable such as a lithium polymer that will provide a power source to the data collection module for which voltage and amperage is sufficient to power the data collection module for a period of time equal to no less than twenty four hours without the need to recharge or replace the power source. In the preferred embodiment of the data collection module a printed circuit board represented schematically in FIG. 19 is configured to couple with the data collection port 122 of the data collection module 110. The on/off switch 120 controls the supply of power to the printed circuit board. A low dropout voltage regulator (not shown) regulates the voltage supplied to the circuitry of the printed circuit board. A central processing unit (CPU) may contain analog to digital converters, memory for signal processing and internal USB circuitry. The printed circuit board is further provided with analog bipolar amplifiers(s), the quantity of which shall be equal to a minimum of one amplifier for each channel of ECG data to be collected and recorded from the physiological sensor device or patch. A non-volatile memory for long term storage is provided, the size of which is adequate to store all data collected during an entire testing period. In addition, depending on the different embodiments of the data collection module, the printed circuit board may include a wireless communications system, such as cellular (CDMA, GSM HSPA +, or LTE), ANT+, Bluetooth, WiFi or WiMax. If a wireless communications system is present on the printed circuit board, then an antenna of the appropriate size and design shall also be present on the printed circuit board or included within the housing of the data collection module.

Regardless of the features contained on the printed circuit board, the printed circuit board is to be constructed in a manner that all embodiments may be housed within a like housing and powered by the same power source so as to utilize the advantages of mass production, to reduce the inventory of parts required and to reduce cost of production and operation.

Figure 21:
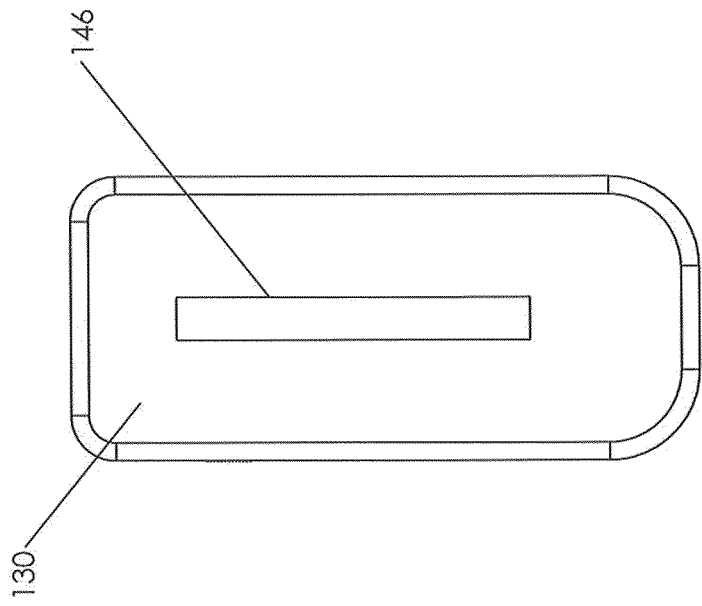
FIG. 21 is a bottom view of the data collection module of FIG. 20.
Figure 20:
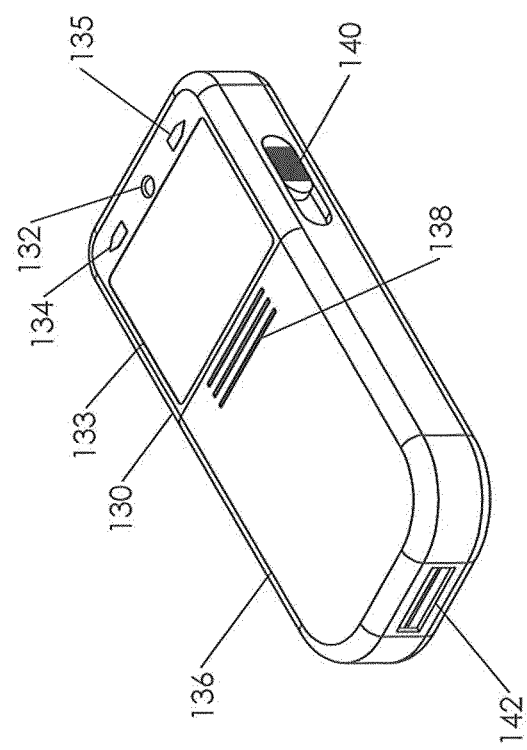
FIG. 20 is a perspective view of a second embodiment of a data collection module.
Figure 22:
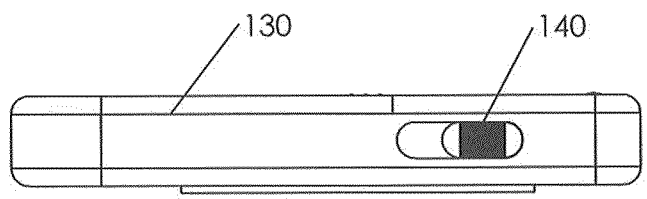
FIG. 22 is a view of a first long side of the data collection module of FIG. 20.
Figure 23:
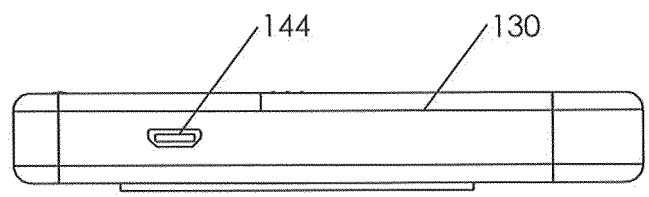
FIG. 23 is a view of a second long side of the data collection module of FIG. 20.
Figure 24:
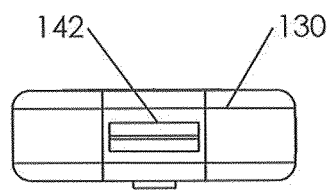
FIG. 24 is a view of a first short side of the data collection module of FIG. 20.
Figure 25:
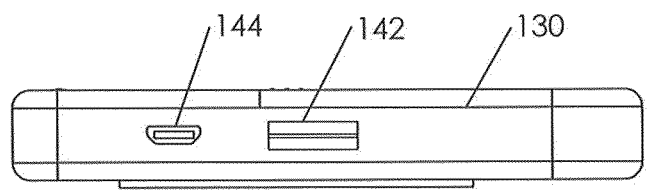
FIG. 25 is a view of a first long side of a second embodiment of a data collection module of FIG. 20.
Figure 26:
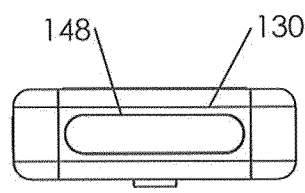
FIG. 26 is a view of a second short side of the data collection module of FIG. 20.

An alternative embodiment of a data collection module 130 is depicted by FIG. 20 thru 26. FIG. 20 is a perspective view of a data collection module according to the alternative embodiment; FIG. 21 is a bottom view of the alternative data collection module; FIG. 22 is a view of a first long side of the alternative data collection module; FIG. 23 is a view of a second long side of the alternative data collection module; FIG. 24 is a view of a first short side of the alternative data collection module; FIG. 25 is a view of a first long side of a second embodiment of alternative data collection module; and FIG. 26 is a view of a second short side of the alternative data collection module. The alternative embodiment of a data collection module 130 is provided with all of the features of the first embodiment 110 including: a multicolor LED 132; a removable cover 136 provided with raised ridges 138 to facilitate removal of the cover; a means 146 for fixing a data collection device to the physiological sensor device or patch; on/off switch 140; a micro USB port 144; a data collection port 142; as well as a power supply and printed circuit board as described above. The data collection module 130 includes additional features that are not part of the first embodiment described above. As shown in FIG. 26 the event button 148 has been moved to a short side of the data collection module 130 at an end of the data collection module opposite the data collection port 142 shown in FIG. 20. A Liquid Crystal Display (LCD) screen 133 has been added to the data collection module 130 along with two user input buttons 134, 135 on the outer surface.

The alternative data collection module 130 allows user interaction with the data collection module for the purposes of acquiring user defined settings or options for the testing procedures being performed by the physiological data collection system. In addition, where communications or alerts from the first embodiment are limited to audible or visual alerts from the multicolor LED 112 in FIG. 13, the LCD display 133 of the alternative data collection module allows descriptive messages, confirmations or alerts to be presented. The user input buttons 134, 135 allow interaction with the programming contained within the CPU of the data collection module as well as communications completed by the transmissions that occur between the remote monitoring and analysis center and the data collection module.

Preferably, prior to the start of a testing period, the data collection module is physically coupled to the physiological sensor device or patch by coupling the common connector 13 of the physiological sensor device or patch with the data collection port 122 of the data collection module 110 to obtain the desired orientation. As shown in FIG. 14 a back side of the data collection module 110 is preferably provided with a means 126 for fixing a data collection module to the physiological sensor device or patch. While any suitable fixing means, including for example an adhesive, may be employed, it is preferred that the fixing means 126 be a component of a hook and loop fastening system. It is preferred that the hook component 126 of the hook and loop fastening system is fixed to the back side of the data collection module to mate with a loop component that is fixed to the front surface of a flexible outer front layer 20 of the physiological sensor device or patch. After the coupling of the common connector 13 of the physiological sensor device or patch with the data collection port 122 of the data collection module 110 is complete, the respective hook and loop portions on the physiological sensor device or patch and the data collection module are joined together to form a physiological data collection system 100. Thereafter, if the physiological sensor device or patch is provided with a rearmost layer 26, 76, 64 that is a removable liner, the removable liner is removed and the physiological data collection system is fixed to the skin of the patient's chest in a manner that is described above. In some embodiments of the physiological sensor device or patch it is necessary to first apply a suitable adhesive to the patient's skin and then fix the physiological data collection system is fixed to the skin of the patient's chest.

It is understood that the data collection module may be attached to the physiological sensor device or patch in either a horizontal or vertical orientation regardless of the patient's gender to allow for increased comfort and concealability during the testing period. It is further understood that when the data collection module is coupled to a physiological sensor device or patch in a horizontal orientation when being used by a female patient the data collection module will be positioned is such a manner that the patient may still wear a brassiere during the testing period without causing any additional discomfort to the female patient.

After the physiological data collection system has been properly affixed to the chest of the patient, the testing period may begin. The physiological data collected via the electrodes of the physiological sensor device or patch worn by the patient during the testing period is collected by the data collection module due to the continuous coupling of the two data collection ports. Analog data from each electrode present in the physiological sensor device or patch is then amplified by bipolar amplifiers contained within the data collection module. The amplified data is then passed to the CPU where analog to digital conversion of the signal takes place so that signal processing may occur and a resulting data stream created. The central processing unit processes the physiological data received in an analog format to be in a format that can be processed and analyzed by using at least one algorithm that is accepted by the medical community for electrocardiograms. The resulting data stream is then passed to the onboard non-volatile long term data storage facility where it will reside until such time as downloading or transmission occurs.

In the preferred embodiment of the invention, transmission of the stored data takes place via a wireless transmission of the processed data to a remote monitoring and analysis center at predefined intervals of time. To protect the privacy and identity of the patient during the testing period, the transmitted data stream only includes the processed data along with a unique identifier that represents the data collection module being used for the test. This process assures that, should data be intercepted or obtained by another source during the transmission period, the data is unusable and unidentifiable to the intercepting party and no violation of patient identity or privacy occurs.

As a backup to and for redundancy purposes, should it be necessary, coupling of a cable between the micro USB port 124 in FIG. 18 and standard USB port present on a personal computer running an application written to obtain data from the data collection module 110 by a manual process may be accomplished. This ensures that should wireless transmission fail or not be available the test is not void and analysis and interpretation of the resulting data may be completed.

Upon successful completion of the testing period, the physiological data collection system 100 is removed from the patient's chest, the data collection module 110 is separated from the physiological sensor device or patch 10 and the physiological sensor device or patch is disposed of. After verification of successful downloading or transmission of the data from the data collection module 110, the data contained within the non-volatile long term storage area is automatically deleted so the data collection module can be returned for future use.

Preferably, the data collection module 110 is a removable, rechargeable and reusable component that is directly coupled to the outer surface of the disposable single use physiological sensor device or patch to be worn on the skin of the patient's chest for a period of time of twenty four to forty eight hours.

After the patient's physiological data that was collected during the testing period has successfully been received at the remote monitoring and analysis facility, analysis, reporting and interpretation occurs. The transferred physiological data collected from the patient during the testing period remains in a raw and unaltered form which allows the data to be subjected to different algorithms or analytical reviews without the need to subject the patient to different testing procedures. In the preferred embodiment of the system the data may be analyzed using an algorithm based on the EASI lead placement method and a complete industry recognized twelve lead ECG report generated. When a physiological sensor device or patch 70 according to the embodiment shown in FIGS. 7-10 is employed to gather data from a patient, the data is analyzed using both the EASI and the MEANS algorithms and comparisons of the resulting reports may be made. The collected data is analyzed, report generated and if necessary interpretation completed. A unique serial number from the data collection module is matched to the corresponding patient in the secure database and an encrypted report is then sent to the ordering practitioner. The data, report and interpretation may then be stored in a long term storage environment for subsequent access in the future should the need arise.

The physiological data collection system 100 is designed to insure the privacy and protection of the patient during the testing period. Prior to the start of the test the unique serial number of the data collection module being used must be married, joined or linked to a patient record contained within a patient management system at a remote monitoring and analysis center. This may be accomplished via a telephonic conversation with a staff member located at the remote monitoring and analysis center, or by means of a secure connection such as a VPN (virtual private network) connecting the ordering practitioners office with the remote monitoring and analysis center for secure and private data entry. Applicable patient information is entered into a secure database located at the remote monitoring and analysis center. This information may include but is not limited to the unique serial number of the data collection module, patient name, ordering practitioner, billing information and required procedures.

The identity, privacy and security of the patient is of paramount concern in the development of the disclosed invention and all precautions are taken to insure this need is met. Physiological data from the patient stored in the data collection module of the physiological data collection system 100 contains no patient identifiable information. Patient data contained within the remote monitoring and analysis center is segregated and secured. Any direct access by the practitioner or a staff member who is accessing or interacting with the data from offsite is done through a secure process such as a VPN connection and reports that are transmitted electronically are encrypted and password protected.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall there between.

What is claimed is:

1. A physiological data collection system comprising in combination a disposable physiological sensor device and a reusable data collection module wherein:
   (a) the disposable physiological sensor device is attachable to the skin of a person for collecting physiological signals generated by the person's body and comprises a flexible front layer comprising a material that does not conduct electricity; a flexible back layer comprising a material that does not conduct electricity, the back layer including a plurality of portals and being provided with an adhesive for adhering the physiological sensor device to the chest of a patient; a flexible intermediate layer comprising a material that does not conduct electricity sandwiched between and fixed to the front layer and the back layer, a plurality of electrodes and electrical conductors are fixed to a back side of the intermediate layer, each of the electrodes is attached to one of the electrical conductors and all of the electrical conductors are attached to a single common connector that protrudes through a portal in the front layer; and a plurality of conductive gel pads, each gel pad adhered to and aligned with and in conductive communication with one of the electrodes and protruding through one of the portals in the back layer; each layer of the physiological sensor device having, when attached to a standing person's chest, a vertically extending portion with a horizontally extending portion located at a lower end of the vertically extending portion and extending to both sides of the vertically extending portion, at least one electrode located in the horizontally extending portion and at least one electrode located higher than the horizontally extending portion when the physiological sensor device is attached to a patient in its' operative location with the patient standing or sitting upright; and
   (b) the reusable data collection module comprises a reusable device having a data collection port for connection to a source of physiological data that is in an analog format, the data collection port being in circuit communication with a plurality of bipolar amplifiers, the bipolar amplifiers being in circuit communication with a central processing unit provided with analog to digital converters, memory for signal processing and internal USB circuitry, the central processing unit being in circuit communication with a means for storing data and with a means for conveying the data in digital form via at least one of a USB port and a wireless communication system;
   the data collection port of the data collection module being coupled to the single common connector, the single common connector being located in the horizontally extending portion of the disposable physiological sensor device and is aligned with the vertically extending portion of the disposable physiological sensor device, the single common connector of the physiological sensor device for transmission of physiological data collected in an analog format by the electrodes of physiological sensor device to the data collection module, and the data collection module being mounted to a front surface of the front layer of the physiological sensor device by a means for fixing the data collection module to the front surface of the front layer of the physiological sensor device.

2. The physiological sensor device of claim 1 wherein the electrodes are disposed to provide placement of the electrodes for acquiring physiological data for analysis and interpretation using an EASI electrocardiogram methodology.

3. The physiological data collection system of claim 1 wherein each layer of the physiological sensor device further comprises a horizontally extending portion located at an upper end of the vertically extending portion and extending to both sides of the vertically extending portion.

4. The physiological data collection system of claim 3 wherein the electrodes are disposed to provide placement of the electrodes for acquiring physiological data for analysis and interpretation using both a MEANS electrocardiogram methodology and an EASI electrocardiogram methodology.

5. The physiological data collection system of claim 3 wherein the central processing unit of the data collection module processes the physiological data received in an analog format to be in a format that can be processed and analyzed by using at least one algorithm that is accepted by the medical community for electrocardiograms.

6. The physiological data collection system of claim 3 wherein the data collection module is provided with a wireless communication system and the transmission of stored processed data takes place via the wireless transmission to a remote monitoring and analysis center at predefined intervals of time.

7. The physiological data collection system of claim 6 wherein the data collection module has a unique serial number that the remote monitoring and analysis center matches to a patient in a secure database and an encrypted report is then sent to a practitioner that ordered the use of the physiological data collection system.

8. The physiological data collection system of claim 1 wherein comfort of the physiological data collection system is enhanced for a female person by the vertically extending portions of the front and back layers having substantially the same width, and the vertically extending portion of the intermediate layer having a width that is less than the widths of the front and back layers to enhance the horizontal flexibility of a vertically extending portion of the physiological sensor device.

9. The physiological data collection system of claim 1 wherein the central processing unit of the data collection module processes the physiological data received in an analog format to be in a format that can be processed and analyzed by using at least one algorithm that is accepted by the medical community for electrocardiograms.

10. The physiological data collection system of claim 1 wherein the data collection module is provided with a wireless communication system and the transmission of stored processed data takes place via the wireless transmission to a remote monitoring and analysis center at predefined intervals of time.

11. The physiological data collection system of claim 10 wherein the data collection module has a unique serial number that the remote monitoring and analysis center matches to a patient in a secure database and an encrypted report is then sent to a practitioner that ordered the use of the physiological data collection system.

12. The physiological data collection system of claim 1 wherein the data collection module has a housing with opposed long sides and opposed short sides and the data collection module is provided with two data collection ports, one located on a long side of the data collection module and the other located on a short side of the data collection module such that the data collection module can be fixed to the physiological sensor device with the long sides oriented either vertically or horizontally.

13. The physiological data collection system of claim 1 wherein the data collection module has a housing with opposed long sides and opposed short sides and the data collection port is located on a short side of the data collection module such that the data collection module can be fixed to the physiological sensor device with the long sides oriented vertically.

14. The physiological data collection system of claim 1 wherein the data collection module may be fixed to the physiological sensor device and the resulting physiological data collection system can be attached to a person's chest by a person who is not skilled or trained by the medical community.

15. A physiological data collection system comprising in combination a disposable physiological sensor device and a reusable data collection module wherein:

(a) the disposable physiological sensor device is attachable to the skin of a person for collecting physiological signals generated by the person's body and comprises a flexible front layer comprising a material that does not conduct electricity; a flexible back layer comprising a material that does not conduct electricity, the back layer including a plurality of portals; a flexible intermediate layer comprising a material that does not conduct electricity sandwiched between and fixed to the front layer and the back layer, a plurality of electrodes and electrical conductors are fixed to a back side of the intermediate layer, each of the electrodes is attached to one of the electrical conductors and all of the electrical conductors are attached to a single common connector that protrudes through a portal in the front layer; and a plurality of conductive gel pads, each gel pad adhered to and aligned with and in conductive communication with one of the electrodes and protruding through one of the portals in the back layer; each layer of the physiological sensor device having, when attached to a standing person's chest, a vertically extending portion with a horizontally extending portion located at a lower end of the vertically extending portion and extending to both sides of the vertically extending portion; and (b) the reusable data collection module comprises a reusable device having a data collection port for connection to a source of physiological data that is in an analog format, the data collection port being in circuit communication with a plurality of bipolar amplifiers, the bipolar amplifiers being in circuit communication with a central processing unit provided with analog to digital converters, memory for signal processing and internal USB circuitry, the central processing unit being in circuit communication with a means for storing data and with a means for conveying the data in digital form via at least one of a USB port and a wireless communication system;

the data collection port of the data collection module being coupled to the single common connector that protrudes through the front layer of the physiological sensor device for transmission of physiological data collected in an analog format by the electrodes of physiological sensor device to the data collection module, and the data collection module being mounted to a front surface of the front layer of the physiological sensor device by a means for fixing the data collection module to the front surface of the front layer of the physiological sensor device, the data collection module having a housing with opposed long sides and opposed short sides and the data collection module is provided with two data collection ports, one located on a long side of the data collection module and the other located on a short side of the data collection module such that the data collection module can be fixed to the physiological sensor device with the long sides oriented either vertically or horizontally.

16. The physiological data collection system of claim 15 wherein the data collection module may be fixed to the physiological sensor device and the resulting physiological data collection system can be attached to a person's chest by a person who is not skilled or trained by the medical community.

17. The physiological data collection system of claim 15 wherein the data collection module is provided with a wireless communication system and the transmission of stored processed data takes place via the wireless transmission to a remote monitoring and analysis center at predefined intervals of time.

18. The physiological data collection system of claim 17 wherein the data collection module has a unique serial number that the remote monitoring and analysis center matches to a patient in a secure database and an encrypted report is then sent to a practitioner that ordered the use of the physiological data collection system.

19. The physiological data collection system of claim 15 wherein comfort of the physiological data collection system is enhanced for a female person by the vertically extending portions of the front and back layers having substantially the same width, and the vertically extending portion of the intermediate layer having a width that is less than the widths of the front and back layers to enhance the horizontal flexibility of a vertically extending portion of the physiological sensor device.

* * * * *